United States Patent
Karaolis

(10) Patent No.: US 7,569,555 B2
(45) Date of Patent: Aug. 4, 2009

(54) METHOD FOR STIMULATING THE IMMUNE, INFLAMMATORY OR NEUROPROTECTIVE RESPONSE

(76) Inventor: David K. R. Karaolis, Oakhaven, Baltimore, MD (US) 21210

( * ) Notice: Subject to any disclaimer, the term of this patent is extended or adjusted under 35 U.S.C. 154(b) by 592 days.

(21) Appl. No.: 11/079,886

(22) Filed: Mar. 15, 2005

(65) Prior Publication Data

US 2006/0040887 A1  Feb. 23, 2006

Related U.S. Application Data

(60) Provisional application No. 60/563,692, filed on Apr. 20, 2004, provisional application No. 60/552,721, filed on Mar. 15, 2004.

(51) Int. Cl.
*A01N 43/04* (2006.01)
*A61K 31/70* (2006.01)
*C07H 19/00* (2006.01)
*C07H 19/22* (2006.01)

(52) U.S. Cl. ............... 514/45; 514/43; 514/48

(58) Field of Classification Search ............ None
See application file for complete search history.

(56) References Cited

FOREIGN PATENT DOCUMENTS

WO  2005030182 A2  4/2005

OTHER PUBLICATIONS

Kawai et al. Nucleic Acids Research Supplement No. 3 (2003), pp. 103-104.*
Steinberger et al. FEBS Letters, vol. 444, No. 1, pp. 125-129, 1999.*
Mayer et al. PNAS USA, vol. 88, pp. 5472-5476, 1991.*
Tischler et al., Cyclic diguanylate (c-di-GMP) regulates Vibrio cholerae biofilm formation, Molecular Microbiology, 53 (3)857-869 (2004).

* cited by examiner

*Primary Examiner*—Patrick T Lewis
(74) *Attorney, Agent, or Firm*—Browdy and Neimark, P.L.L.C.

(57) ABSTRACT

Cycic di-GMP, or a cyclic dinucleotide analogue thereof that has the same effect as cyclic di-GMP, stimulates or enhances immune or inflammatory response in a patient or enhances the immune response to a vaccine by serving as an adjuvant. Cyclic di-GMP, or a cyclic dinucleotide analogue thereof, also has neuroprotective properties for use as a neuroprotective agent to inhibit, treat, or ameliorate the effects of injuries, diseases, disorders or conditions that result in neurodegeneration.

17 Claims, 5 Drawing Sheets

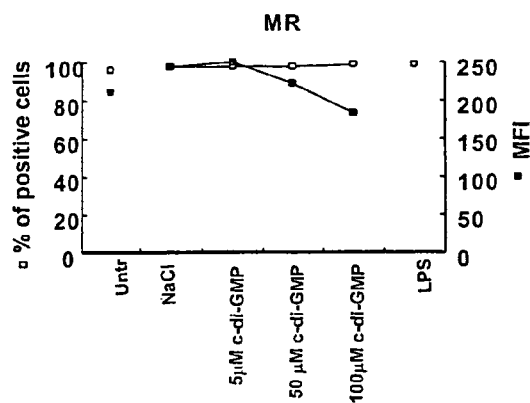
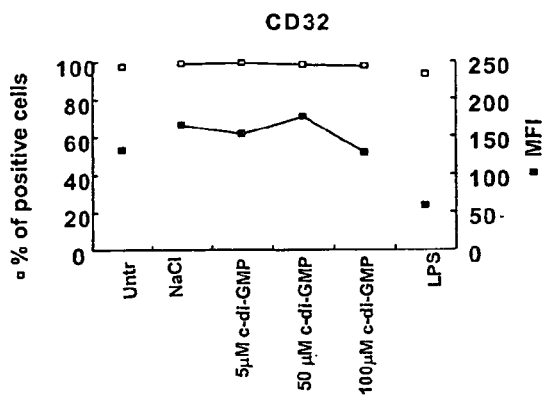
FIG. 1G  FIG. 1H
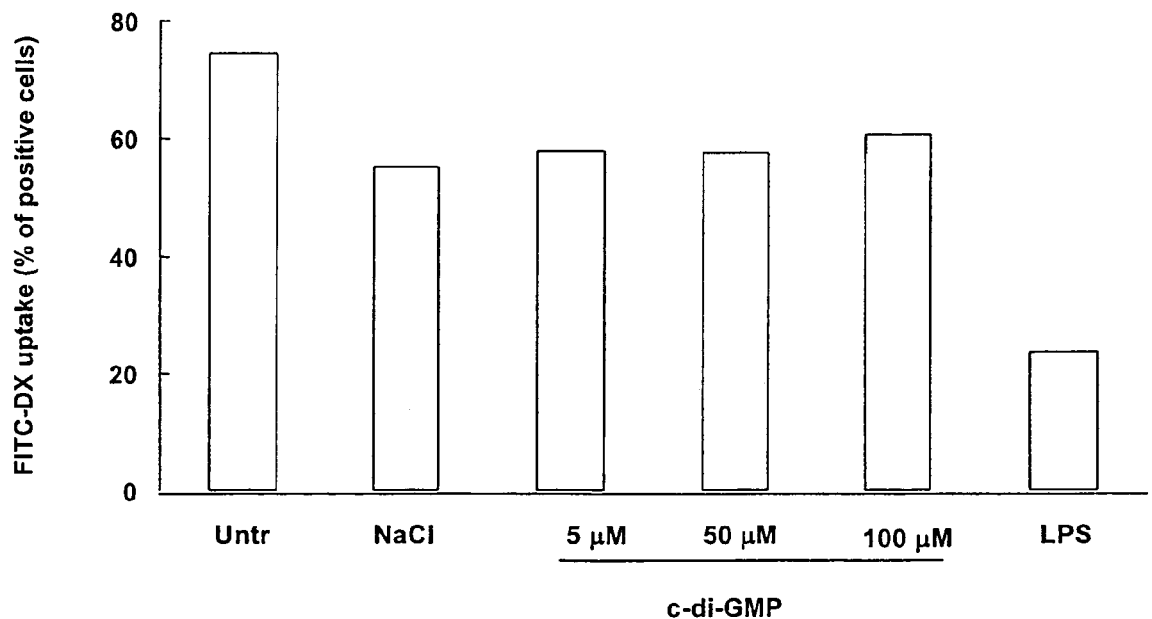
FIG. 2

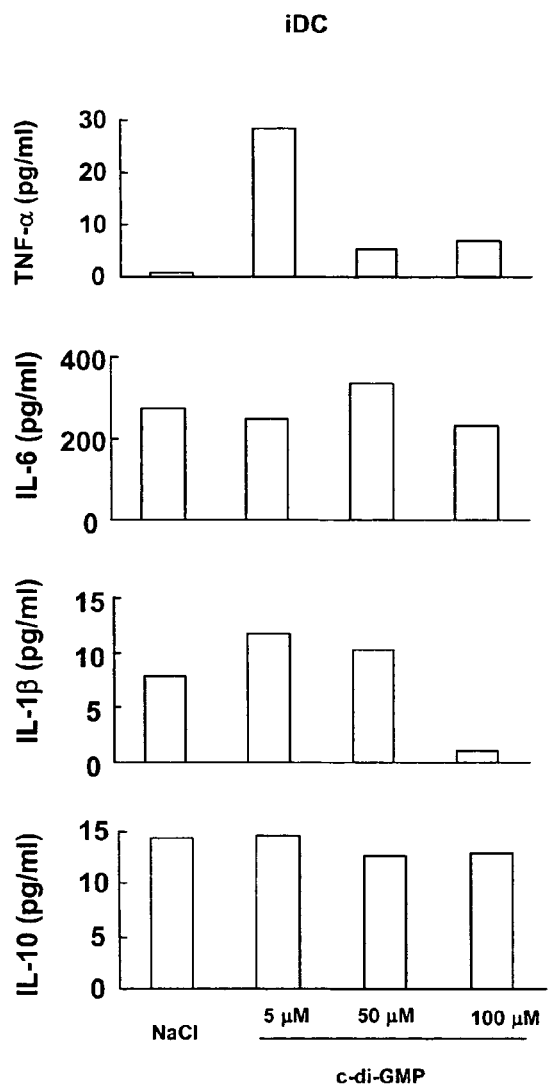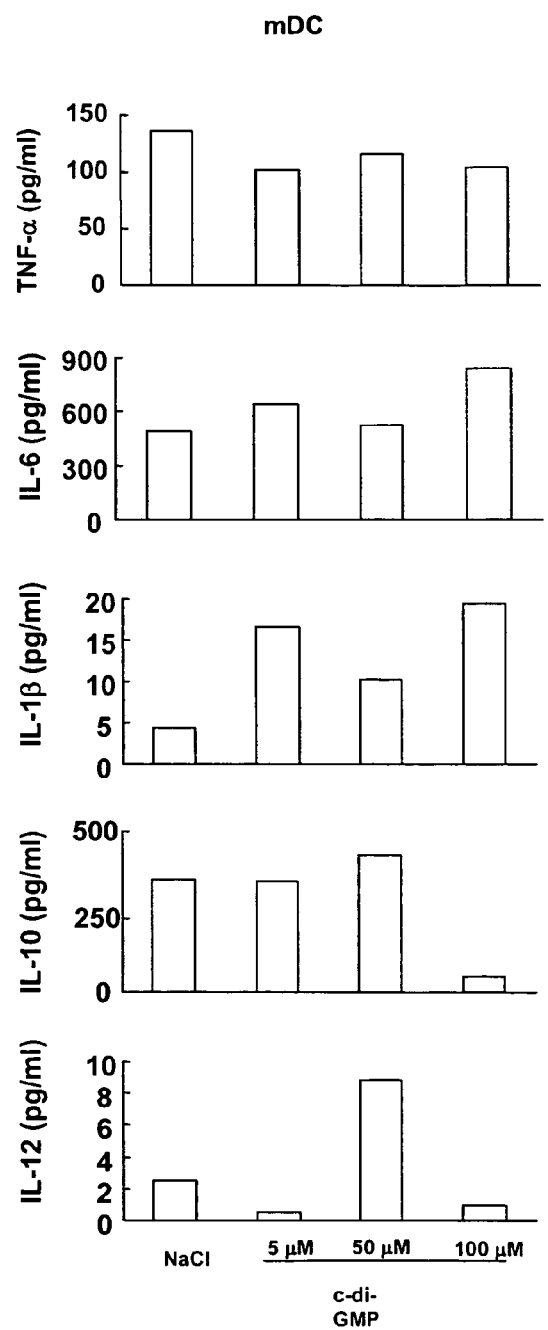
FIG. 3A
FIG. 3B

METHOD FOR STIMULATING THE IMMUNE, INFLAMMATORY OR NEUROPROTECTIVE RESPONSE

CROSS-REFERENCE TO RELATED APPLICATIONS

This application claims the benefit of priority under 35 U.S.C. §119(e) from U.S. provisional application Nos. 60/552,721, filed Mar. 15, 2004, and 60/563,692, filed Apr. 20, 2004, the entire contents of which are hereby incorporated by reference.

BACKGROUND OF THE INVENTION

1. Field of the invention

The present invention relates to immunomodulation and to the stimulation and enhancement of the immune or inflammatory response, including the use of adjuvants to enhance immune response to a vaccine. The present invention also relates to treatment of injuries, diseases, disorders and conditions that result in neurodegeneration.

2. Description of the Related Art

Millions worldwide are affected with infectious diseases, cancer, lymphomas, HIV, AIDS, rheumatoid arthritis, asthma, immunodeficiency disorders and diseases involving defective immune, allergic, or inflammatory responses. Many diseases and their disease outcomes involve immune or inflammatory responses and are associated with the stimulation of dendritic cells (DCs), T cells, the production or suppression of various cytokines, chemokines and interferons, and the increase or decrease in the availability of cytokines and chemokine receptors. In addition, many neurological and neurodegenerative diseases involve damage to nerve or neuronal cells.

Dendritic Cells

Dendritic cells (DCs) are the most potent antigen-presenting cells and they play a crucial role in the generation and regulation of immunity (Bancherau and Steinman, 1998; Sallusto and Lanzavecchia, 1994). Their priming ability is acquired upon maturation and is characterized by the activation of transcription factors, antigen processing, control of migration and regulation of inflammatory responses (Shutt et al., 2000; Granucci et al., 2001; Sallusto et al., 1999; Ouaaz et al., 2002). Regulated migration of DCs is central to the induction of physiological immune responses. The expression of surface molecules on DCs known to be critical for antigen-presenting function include HLA-DR, CD40, CD83, CXCR4 and CD80 and CD86 and this is associated with increased cytokine and chemokine production and stimulatory capacity.

DCs link innate and adaptive immunity by sensing pathogens or vaccinogens and signaling a variety of defense responses. DCs comprise a family of cells specializing in antigen capture and presentation to T cells, play a role in bacterial uptake across mucosal surfaces, can open tight junctions and sample antigens directly across epithelia (Rimoldi et al., 2004). DCs sample enteric antigens in the lamina propria and Peyer's patches, and transport them to mesenteric nodes where they are presented to lymphocytes (Macpherson et al., 2004). DCs are potent antigen-presenting cell that are able to initiate and modulate immune responses and are hence often exploited as cellular vaccine components for applications such as immunotherapy. Their ability to migrate from peripheral tissues to the T cell areas of draining lymph nodes is crucial for the priming of T lymphocytes. Signal molecules that promote DCs to acquire potent Th-1 cell stimulatory activity and substantial chemotactic responsiveness to chemokines would be useful in the development of vaccines and for tumor immunotherapy (Scandella et al., 2002).

DCs are the first target of HIV and, by clustering and activating T cells, may both activate antiviral immunity and facilitate virus dissemination (Sewell and Price, 2001; Frank and Pope, 2002). During HIV infection, there is loss of immune control and dysfunction of DCs may contribute to immune suppression associated with AIDS progression (Quaranta et al., 2004). Activation of immature DCs by manipulating their phenotypical, morphological and functional developmental program would have useful clinical applications for therapeutic intervention for AIDS patients.

Cytokines and Costimulatory Molecules

Cytokines are proteins that regulate immune and inflammatory reactions. Cytokines play an essential role in the activation and maintenance of both innate and acquired immune responses. Cytokines and chemokines have been used as vaccine adjuvants with both traditional and DNA vaccines. Cytokines are small proteins (~25 kDa) that are released by various cells in the body, usually in response to an activating stimulus, and induce responses through binding to specific receptors. They can act in an autocrine manner, affecting the behavior of the cell that releases the cytokine, or in a paracrine manner, affecting the behavior of adjacent cells. Some cytokines can act in an endocrine manner, affecting the behavior of distant cells, although this depends on their ability to enter the circulation and on their half-life.

Interleukin-12 (IL-12) is a potent enhancer of cellular responses. IL-12 is a potent proinflammatory cytokine with potent antitumor effects that enhances cytotoxic T lymphocytes (CTL) and natural killer (NK) cell activity. IL-12 treatment of mice augments antibody responses to T independent polysaccharide antigen (Buchanan et al., 1998). IL-12 and IL-1 have been shown to induce systemic immunity to mucosally administered vaccines (Boyaka and McGhee, 2001). Studies have shown the regression of established neuroblastoma in mice vaccinated with IL-12 transduced dendritic cells (Redlinger et al., 2003). Another study with syngeneic A/J mice using intratumorally injected IL-12 transduced cells showed that mice underwent tumor regression indicating that increased IL-12 production by DCs induces a significant antitumor response in a poorly immunogenic murine model of neuroblastoma (Shimizu et al., 2001). These results clearly show the vital role of DCs in the immunobiology of neuroblastoma, and that protection of these cells from tumour induced apoptosis is a critical aspect for immunotherapies treating aggressive tumors. Co-expression of cytokines, chemokines and costimulatory molecules enhances the immunogenicity of DNA vaccines.

As is true for most intracellular pathogens, immunization with live *Chlamydia trachomatis* induces a stronger protective immunity than immunization with inactivated organism and is associated with high levels of the proinflammatory cytokine IL-12 and the enrichment of DCs among mice immunized with viable organisms (Zhang, et al., 1999). These results indicate that the induction of proinflammatory cytokines and activation and differentiation of DCs is important for inducing active immunity to *C. trachomatis* infection.

Chemokines are a class of cytokines that have chemoattractant properties, inducing cells with the appropriate receptors to migrate toward the source of the chemokine. Certain chemokines may recruit cells to sites of infection. Chemokines such as RANTES may promote the infiltration into tissues of a range of leukocytes including effector T cells. Effector T cells that recognize pathogen antigens in the tissues produce cytokines such as TNF-α, which activates endothelial cells to express E-selectin, VCAM-1, and ICAM-1, and chemokines such as RANTES, which can then act on effector T cells to activate their adhesion molecules.

Chemokines exert their effects through at least nineteen G protein-coupled receptors (GPCRs). The nomenclature of the chemokine receptors follows the notation used for the chemokine subfamilies and they are termed CCR1-10 (CC chemokine receptor 1-10), CXCR1-6, XCR1 and CX3CR1. A remarkable feature of the chemokine receptors is their relative lack of selectivity in ligand binding, with many chemokine receptors binding more than one chemokine with high affinity. For example, eleven chemokines are reported to bind to the CCR1 receptor, including MIP-1α (macrophage inflammatory protein 1α), MIP-1β, MIP-1δ, RANTES (regulated on activation normal T cell expressed and secreted), MCP-1 (monocyte chemotactic peptide 1), MCP-2, MCP-3, MCP-4, Lkn-1 (leukotactin-1), MPIF-1 (myeloid progenitor inhibitory factor 1) and HCC-1 (hemofiltrate CC chemokine 1), with varying affinities and acting with different degrees of agonism. Similarly, individual chemokines act as ligands for different receptors. For example, MCP-3 acts as a ligand for CCR1, CCR2, CCR3 and CCR5. This promiscuity and the apparent redundancy of signaling that may arise poses many questions as to the control of chemokine signaling in different tissues expressing different combinations of chemokines, receptors and effectors (*ACTA BIOCHIMICA et BIOPHYSICA SINICA* 2003, 35(9):779-788).

There are different variants of HIV, and the cell types that they infect are determined to a large degree by which chemokine receptor they bind as co-receptor. The variants of HIV that are associated with primary infections use CCR5, which binds the CC chemokines RANTES, MIP-1α, and MIP-1β, as a co-receptor, and require only a low level of CD4 on the cells they infect. These variants of HIV infect dendritic cells, macrophages, and T cells in vivo.

Despite the apparent complexities of the chemokine signaling systems, the importance of individual chemokine receptors is gradually emerging from detailed studies on knockout mice, targeted gene disruption and the application of specific chemokine antagonists. As an example, CCR1 knockout mice have been reported to have disordered trafficking and proliferation of myeloid progenitor cells and to display impaired inflammatory responses to a variety of stimuli. Control of the CCR1 signaling system was demonstrated to have clinical significance as CCR1 knockout mice display significantly reduced rejection responses to cardiac allografts. This suggests that a strategy of blocking CCR1 signaling pathways may be useful in preventing rejection of transplanted tissues (*ACTA BIOCHIMICA et BIOPHYSICA SINICA* 2003, 35(9):779-788).

CCR5 has generated widespread interest because of its role as a co-receptor for HIV. The identification of a naturally occurring mutant of this receptor, CCR5Δ32, and observations that homo and heterozygotes for this mutant have increased resistance to HIV infection and the development of AIDS has highlighted the potential benefits to human health that could accrue from controlling the ability of CCR5 to bind ligands (*ACTA BIOCHIMICA et BIOPHYSICA SINICA* 2003, 35(9):779-788).

Immunotherapy

Costimulatory molecules are important regulators of T cell activation and thus are the favored targets for therapeutic manipulation of the immune response. One of the key costimulatory receptors is CD80, which binds T cell ligands, CD28, and CTLA-4. It has been shown that expression of the costimulatory molecules CD80, CD86 and CD83 plays an important role in adjuvant activity and it is known that expression of CD86 is a feature of CT-based adjuvants (Lyke, 2004). Thus, molecules or compounds that affect CD80 expression represent promising novel therapeutic and immunotherapy agents that might induce protective immunity. A number of immunomodulatory therapies are being developed for clinical applications. These include approaches targeting antigen presentation and costimulation, T cell activation, action of proinflammatory mediators and modulating the cytokine balance (Asadullah et al., 2002). Tumor necrosis factors (TNFs) are known to be cytotoxic cytokines produced by macrophages and lymphocytes and are found to be suppressed in cancer patients or those who are pregnant.

Immunotherapy for Cancer

Immunosuppression is a hallmark of advanced malignancies in man (Lentz, 1999). Immunotherapy is the name given to cancer treatments that use the immune system to attack cancers. That is, the immune system can be stimulated to slow down the growth and spread of cancer. Immunotherapies involving certain cytokines and antibodies have now become part of standard cancer treatment. Immunotherapy of cancer began approximately 100 years ago when Dr. William Coley showed that cancer could be controlled by injections of bacterial products and components known as Coley's toxin. It is now known that the active anti-cancer component of Coley's toxin are bacterial oligonucleotides.

Systemic immunotherapy refers to immunotherapy that is used to treat the whole body and is more commonly used than local immunotherapy which is used to treat one "localized" part of the body, particularly when a cancer has spread. The suppressive milieu present within established tumors inhibits effective immune responses and new strategies are emerging to manipulate the local tumor environment to promote a proinflammatory environment, promote dendritic cell activation, and enhance antitumor immunity (Kaufman and Disis, 2004).

Immunotherapy is a potential useful strategy for the treatment of brain tumors because it offers a degree of specificity, the ability to extravasate into solid tumors, and the potential for eliciting a long-term protective immune response. Several approaches have been developed including the use of cytokines. In studies on the treatment of brain tumors, T cell stimulation with the proinflammatory cytokine IL-12 can elicit antitumor immunity (Gawlick et al., 2004). As such, cytokine treatments combined with tumor-targeted costimulation, or methods that stimulate cytokine production and the proinflammatory response, may be a useful adjunct treatment for brain tumors.

Immunotherapy for Infectious Diseases

In order to combat the increasing prevalence of drug-resistant *Mycobacterium tuberculosis* infection, new drugs are being developed. One promising strategy is to treat patients with refractory mycobacteriosis using ordinary antimycobacterial drugs in combination with appropriate immunomodulators in order to mobilize the cytokine network in response to mycobacterial infection such as using immunomodulating cytokines (especially Th-1 and Th-1-like cytokines such as IL-12 and proinflammatory cytokines such as TNF-α (Tomioka 2004). The Th-1 response participates in cell-mediated immunity and is essential in controlling infections due to intracellular pathogens and viruses.

Although *Cryptococcus neoformans* is a fungal pathogen that causes human disease predominantly in the immunocompromised host, severe infection can occur in immunocompetent individuals. Activation of cellular immunity plays a key role in anticryptococcal defense, and therefore, immunotherapy to increase the immune and proinflammatory response would be a useful treatment to restore immunological parameters and sustained clinical recovery for refractory cryptococcal meningitis (Netea et al., 2004).

The bacterium *Bacillus anthracis* causes the disease anthrax, which if left untreated, can result in bactermia, multisystem dysfunction and death. Anthrax lethal toxin severely impairs the function of dendritic cells-which are pivotal to the establishment of immunity against pathogens- and host immune responses (Agrawal et al., 2003). Dendritic cells exposed to lethal toxin and then exposed to lipopolysaccharide do not upregulate costimulatory molecules, secrete greatly diminished amounts of proinflammatory cytokines, and do not effectively stimulate T cells (Agrawal et al., 2003). Methods to stimulate dendritic cells and the proinflammatory response might be a useful strategy to stimulate the immune response and in the immunotherapy of anthrax infection.

Host defenses against systemic mycoses is multifactorial, depending on innate, as well as acquired mechanisms in which innate resistance includes inflammatory responses whereby production of proinflammatory cytokines increase the capacity of host defenses for killing (Clemons and Stevens, 2001). Therefore, a strong Th-1 response can provide protective immunity suggesting that immunotherapy has utility as a basis in treating or inhibiting mycoses.

Studies on the intracellular activities occurring during *Salmonella* infection in DCs show that the bacteria suppress T cell proliferation (Cheminay et al., 2005). This suggests that immunotherapy might be a useful approach in the inhibition or treatment of infections caused by intracellular bacteria such as *Salmonella*.

Chemokines that bind to HIV co-receptors are potent and selective inhibitors of HIV infection and can be used in controlling HIV infection in concert with humoral and cellular immune and inflammatory responses (Garzino-Demo et al., 2000). This indicates that methods or molecules that promote the immunostimulation of chemokines can be used to inhibit or treat HIV infection.

Oligonucleotide Molecules as Anti-Cancer Agents

The use of unmethylated (CpG) oligonucleotides in the treatment or prevention of cancer has been reported. Synthetic oligonucleotides containing CpG with appropriate flanking regions (CpG motif) have been found to activate macrophages, dendritic cells and B cells to secrete a variety of immunomodulatory cytokines such as IL-6, IL-12, IL-18 and gamma interferon (Krieg, 2002). CpG DNA has also been shown to activate costimulatory molecules such as CD80 and CD86. CpG DNA induces strong innate immunity at mucosal surfaces. The immunostimulatory property of CpG DNA produces long-term vaccine-like effects due to its adjuvant properties. CpG oligonucleotides influence both antibody and cell-mediated immunity and applications include vaccine adjuvants, taming allergic reactions and potentiating monoclonal antibodies and cytotoxic immune cells. They also enhance the antitumor effects of chemotherapeutic agents and improve survival after surgical section of a solid tumor (Weigel et al., 2003). For CpG oligonucleotides, the anti-tumor effect is mediated via activation of the host immune system, not through direct anti-tumor effects. Data demonstrate that systemic application of proinflammatory reagents drastically enhances extravasation of effector cells into tumor tissue, an observation that is of general importance for immunotherapy of solid tumors in a clinical setting (Garbi et al., 2004). Based on their immunotherapeutic properties, CpG oligonucleotides have been used to treat and prevent various cancers and used in cancer vaccines. (U.S. Pat. Nos: 6,653, 292; 6,429,199; 6,406,705; and 6,194,388).

Immunotherapy for Neurodegenerative Disease

The nervous system comprises the central and the peripheral nervous system. The central nervous system (CNS) is composed of the brain and spinal cord and the peripheral nervous system (PNS) consists of all of the other neural elements, namely the nerves and ganglia outside of the brain and spinal cord.

Damage to the nervous system may result from a traumatic injury, such as penetrating trauma or blunt trauma, or a disease or disorder, including but not limited to Alzheimer's disease, Parkinson's disease, Huntington's disease, amyotrophic lateral sclerosis (ALS), diabetic neuropathy, senile dementia, and ischemia.

Maintenance of central nervous system integrity is a complex "balancing act" in which compromises are struck with the immune system. In most tissues, the immune system plays an essential part in protection, repair, and healing. In the central nervous system, because of its unique immune privilege, immunological reactions are relatively limited (Streilein, 1993 and 1995). A growing body of evidence indicates that the failure of the mammalian central nervous system to achieve functional recovery after injury is a reflection of an ineffective dialog between the damaged tissue and the immune system. For example, the restricted communication between the central nervous system and blood-borne macrophages affects the capacity of axotomized axons to regrow; transplants of activated macrophages can promote central nervous system regrowth (Lazarov Spiegler et al, 1996; Rapalino et al, 1998).

Activated T cells have been shown to enter the central nervous system parenchyma, irrespective of their antigen specificity, but only T cells capable of reacting with a central nervous system antigen seem to persist there (Hickey et al, 1991; Werkele, 1993; Kramer et al, 1995). T cells reactive to antigens of central nervous system white matter, such as myelin basic protein (MBP), can induce the paralytic disease experimental autoimmune encephalomyelitis (EAE) within several days of their inoculation into naive recipient rats (Ben-Nun, 1981a). Anti-MBP T cells may also be involved in the human disease multiple sclerosis (Ota, K. et al, 1990; Martin, 1997). However, despite their pathogenic potential, anti-MBP T cell clones are present in the immune systems of healthy subjects (Burns, 1983; Pette, M. et al, 1990; Martin et al, 1990; Schluesener et al, 1985). Activated T cells, which normally patrol the intact central nervous system, transiently accumulate at sites of central nervous system white matter lesions (Hirschberg et al, 1998).

A catastrophic consequence of central nervous system injury is that the primary damage is often compounded by the gradual secondary loss of adjacent neurons that apparently were undamaged, or only marginally damaged, by the initial injury (Faden et al, 1992; Faden 1993; McIntosh, 1993). The primary lesion causes changes in extracellular ion concentrations, elevation of amounts of free radicals, release of neurotransmitters, depletion of growth factors, and local inflammation. These changes trigger a cascade of destructive events in the adjacent neurons that initially escaped the primary injury (Lynch et al, 1994; Bazan et al, 1995; Wu et al, 1994). This secondary damage is mediated by activation of voltage-dependent or agonist-gated channels, ion leaks, activation of calcium-dependent enzymes such as proteases, lipases and nucleases, mitochondrial dysfunction and energy depletion, culminating in neuronal cell death (Yoshina et al, 1991;

Hovda et al, 1991; Zivin et al, 1991; Yoles et al, 1992). The widespread loss of neurons beyond the loss caused directly by the primary injury has been called "secondary degeneration."

One of the most common mediators which cause self-propagation of the diseases even when the primary risk factor is removed or attenuated is glutamate, an excitatory amino acid capable of displaying dual activity: playing a pivotal role in normal central nervous system (CNS) functioning as an essential neurotransmitter, but becoming toxic when its physiological levels are exceeded. Elevation of glutamate has been reported in many CNS disorders. In its role as an excitotoxic compound, glutamate is one of the most common mediators of toxicity in acute and chronic (including optic nerve degeneration in glaucoma) degenerative disorders (Pitt et al., 2000 and Schoepp et al., 1996). Endogenous glutamate has been attributed to the brain damage occurring acutely after status epilepticus, cerebral ischemia or traumatic brain injury. It may also contribute to chronic neurodegeneration in such disorders as amyotrophic lateral sclerosis and Huntington's chorea.

Intensive research has been devoted to attenuating the cytotoxic effect of glutamate by the use of locally acting drugs, such as NMDA-receptor antagonists (Brauner-Osborne et al., 2000). Conventional therapy of this type is often unsatisfactory, however, as in neutralizing the toxic effect it is likely to interfere with the physiological functioning. In humans, such compounds have psychotropic and other side effects that make them unsuitable as therapeutic agents. They also have the disadvantage of interfering with the essential physiological functioning of glutamate as a ubiquitous CNS neurotransmitter. Because glutamate activity is essential for normal physiological functioning, yet is potentially devastating after acute injury or in chronic CNS disorders, any attempt to neutralize its harmful effect must do so without eliminating its essential activity at other sites in the body.

Another tragic consequence of central nervous system injury is that neurons in the mammalian central nervous system do not undergo spontaneous regeneration following an injury. Thus, a central nervous system injury causes permanent impairment of motor and sensory functions.

Spinal cord lesions, regardless of the severity of the injury, initially result in a complete functional paralysis known as spinal shock. Some spontaneous recovery from spinal shock may be observed, starting a few days after the injury and tapering off within three to four weeks. The less severe the insult, the better the functional outcome. The extent of recovery is a function of the amount of undamaged tissue minus the loss due to secondary degeneration. Recovery from injury would be improved by neuroprotective treatment that could reduce secondary degeneration. For example, alleviation of the effect of glutamate is a frequent target of neuroprotective drug development. Among the drugs which are being developed for this purpose are N-methyl-D-aspartate (NMDA)-receptor or alpha-amino-3-hydroxy-5-methyl-4-isoxazoleproprionic acid (AMPA)-receptor antagonists. These drugs will inevitably have severe side effects as they interfere with the functioning of NMDA and AMPA receptors, which are crucial for CNS activity. One of the most intensely studied NMDA-receptor antagonists is MK801, which provides effective neuroprotection but with severe side effects. In animal models of cerebral ischemia and traumatic brain injury, NMDA and AMPA receptor antagonists protect against acute brain damage and delayed behavioral deficits. Such compounds are undergoing testing in humans, but therapeutic efficacy has yet to be established. Other clinical conditions that may respond to drugs acting on glutamatergic transmission include epilepsy, amnesia, anxiety, hyperalgesia and psychosis (Meldrum, 2000).

Glaucoma may be viewed as a neurodegenerative disease and consequently amenable to any therapeutic intervention applicable to neurodegenerative diseases. There is evidence that neuroprotection can be achieved both pharmacologically and immunologically where immunologic intervention boosts the body's repair mechanisms for counteracting the toxicity of physiologic compounds acting as stress signals and that boosting of a T cell-based mechanism promotes recovery of the damaged optic nerve. (Schwartz, 2003; Schwartz, 2004).

In rat cerebral cortical cultures, neuronal killing was partially or completely prevented by chemokines that stimulate the CXCR4, CCR3 or CCR5 chemokine receptors (Brenneman et al., 1999). Cytokines have been shown to be involved in nerve regeneration (Stoll et al., 2000).

Vaccines and Adjuvants

Vaccination is the single most valuable tool in the prevention of disease caused by infectious agents. Vaccination to protect against various infectious diseases may be enhanced by using adjuvants that can selectively stimulate immunoregulatory responses. Compared to injection of an antigen alone, injection of antigen plus an adjuvant generally permits use of a much smaller quantity of antigen and increases the antibody titer. Attenuated viruses and recombinant proteins are poorly immunogenic and absolutely require adjuvants for efficient immunostimulation, as do other antigens such as synthetic peptides, subunit vaccines, polysaccharides, killed cell preparations and plasmid DNA. For example, tetanus toxoid is not immunogenic in the absence of adjuvants. Some of these antigens require high production costs due to purification processes that are necessary to avoid contamination from cell products. The adjuvant may aid the immune response by forming a depot of antigen at the site of interest, it may serve as a vehicle to help deliver the antigen to the spleen or lymph nodes where antigen is trapped by follicular DCs, or it may activate the various cells involved in the immune response, either directly or indirectly. Many bacteria contain substances or products (e.g., endotoxin or cell wall constituents) that activate cells of the immune system. Safe and potent new adjuvants are needed for vaccines. These include vaccines that are administered at mucosal surfaces. The development of methods to enhance antigen presentation by DC is required for successful vaccines, particularly in immunocompromised patients. Activation of DCs is crucial for priming cytotoxic T lymphocytes (CTL), which have a critical role in tumor immunity, and it is considered that adjuvants are necessary for activation of DCs and for enhancement of cellular immunity. A Th-1 oriented immune response is important for an adequate cell mediated immune response and for protection induced by natural infection or vaccination with vaccines. Desirable properties of an adjuvant other than a strong and sustained immunostimulatory ability that should be considered are its safety, biodegradability, stability, ease of mixing and use, broad range of antigens and administration routes that can be used, and its economical manufacture.

A number of adjuvants have been developed. Complete Freund's adjuvant (FCA) is a mixture of a non-metabolizable oil (mineral oil), a surfactant, and killed mycobacterial cells and has been used for many years to enhance the immunologic responses to antigens. Although FCA is effective for production of antibodies, there are problems and hazards associated with its use including a chronic inflammatory response at the site of injection that may be severe and painful which might result in granulomas (Broderson, 1989). FCA is also a hazard for laboratory personnel (Chapel and August, 1976). Incomplete Freund's adjuvant (FIA) does not contain any mycobacterial and while it shows adjuvant properties, it is considered less potent than FCA. A number of experimental adjuvants have been reported in recent years (McCluskie and Weeratna, 2001) which include: bacterial toxins such as cholera toxin (CT), *Escherichia coli* labile toxin (LT), IL-12, LPS-derivatives, and oligonucleotides containing CpG motifs. Their mode of action differ but include: a) enhancement of immunological half-life of the co-administered vaccine antigen; b) increased antigen uptake and presentation; and c) modulatory effects on the production of immunomodulatory cytokines resulting in the preferential development of certain types of immune responses (e.g. Th-1 versus Th-2, mucosal, cell mediated, etc). Adjuvants can be classified into two groups: i) immunostimulatory molecules such as CpG oligonucleotides, bacterial toxins and derivatives, the lipopolysaccharide derivative lipid A, cytokines and hormones; and ii) delivery systems which possess inherent immunostimulatory activity such as liposomes, emulsions, microparticles.

With cancer vaccines, the objective is to get the body to elicit its own immune response. Cancer vaccines would typically consist of a source of cancer-associated material or cells (antigen) that may be autologous (from self) or allogenic (from others) to the patient, along with other components (e.g., adjuvants) to further stimulate and boost the immune response against the antigen. Cancer vaccines cause the immune system to produce antibodies to one or several specific antigens, and/or to produce killer T cells to attack cancer cells that have those antigens. T cells in the body react with cancer cells so stimulation of a patient's T cells would increase the ability of T cells to recognize cancer cells. In addition, dendritic cells which are specialized antigen presenting cells, help the immune system to recognize cancer cells by presenting cancer antigens to T cells, making it easier for the immune system cells to react with and attack them. Dendritic cells are the most effective antigen-presenting cells known. Dendritic cells link innate immunity and adaptive immunity. Dendritic cells can efficiently present cancer proteins to activate the immune response, so agents that activate or turn on dendritic cells and the immune response, have clinical applications in preventing or treating cancer and in immunotherapy.

Studies on antitumor immunity have shown that a nontoxic cholera toxin subunit can up-regulate the secretion of IL-12 from DCs suggesting DC maturation and that this molecule acts as an adjuvant to enhance immunity through DC maturation and may be considered a useful adjuvant to raise immunity in a clinical application (Isomura et al., 2005). IL-12 can act as a mucosal adjuvant for coadministered antigens. Studies have shown that proinflammatory cytokines such as IL-12 can replace cholera toxin (CT) as a mucosal adjuvant for antibody induction and are important candidates for use as mucosal adjuvants with HIV and other vaccines (Bradney et al., 2002).

DNA containing an unmethylated CpG motif (CpG oligonucleotides) are a potent immunostimulator and can trigger innate immune responses which promote the combating of infection. oligonucleotides containing unmethylated CpG motifs act as immune adjuvants, accelerating and boosting antibody responses promoting the production of Th-1 proinflammatory cytokines and inducing the maturation/activation of DCs (Klinman, 2003). CpG oligonucleotides have become a promising immunotherapeutic candidate to assist and direct immune responses such as vaccination or modulation of allergic responses (Dalpke, et al., 2002). CpG oligonucleotides are a strong inducer of IL-12 indicating that it acts as a Th-1 polarizing agent that can be utilized as a potent vaccine adjuvant (Dalpke et al., 2002). Infection such as those caused by intracellular bacteria and viruses, induces innate immunity by causing the infected cells to produce proinflammatory cytokines that directly combat bacterial invaders and to express costimulating surface molecules, which develop adaptive immunity by inducing T cell differentiation. CpG DNA immunostimulatory responses are consistent between in vitro and in vivo studies (Zelenay et al., 2003). Coadministration of CpG DNA with a variety of vaccines has improved protective immunity in animal challenge models and are safe and well-tolerated (Klinman, 2003). A study addressing tumor immune therapy has shown that stimulation of T helper cells with syngeneic tumor cells and antigen-presenting cells in the presence of CpG DNA allows the generation of large numbers of strongly polarized, tumor-specific Th-1 cells, indicating the eradication of established tumors and lymphoma by activating proinflammatory responses and based on this immunostimulatory ability, has clinical utility in immunotherapy (Egeter et al., 2000).

While certain treatments for infectious diseases, cancer, immunodeficiciency and inflammatory disorders and neurological and neurodegenerative diseases are available, improved treatments are needed. Also needed are the development of improved vaccines for a variety of diseases through the use of better vaccine adjuvants.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method of stimulating and/or modulating the immune and inflammatory response such as a method for stimulating or enhancing immune or inflammatory response or for preventing or treating allergic reactions (e.g., asthma) in a patient which involves administering an effective amount of cyclic di-GMP or a cyclic dinucleotide analogue thereof to a patient in need thereof. Encompassed by this method is enhancement of immune response to a vaccine by administering an effective amount of cyclic di-GMP or a cyclic dinucleotide analogue thereof serving as an adjuvant for the administered vaccine.

The present invention also provides a method for stimulating or enhancing an immune response in a patient by activating dendritic cells or T cells with antigen and with cyclic di-GMP or a cyclic dinucleotide analogue thereof prior to administering the activated dendritic cells or T cells as a cellular vaccine to a patient.

Further provided by the present invention is a method for inhibiting, treating or ameliorating the effects of an injury, disease, disorder, or condition that result in neuronal degeneration by administering to a patient in need thereof an effective amount of cyclic di-GMP or a cyclic dinucleotide analogue thereof to inhibit, treat or ameliorate the effects of the injury, disease, disorder, or condition that result in neuronal degeneration.

Additional aspects of the present invention include a pharmaceutical composition for stimulating or enhancing immune or inflammatory response containing cyclic di-GMP or a cyclic dinucleotide analogue thereof and an immunizing composition containing a vaccine and cyclic di-GMP or a cyclic dinucleotide analogue thereof.

BRIEF DESCRIPTION OF THE DRAWINGS

FIGS. 1A-1H are graphs of the surface phenotype of DCs exposed to c-di-GMP. DCs were left untreated (Untr) or were treated with NaCl, c-di-GMP or LPS for 24 h. DCs were then analysed for expression of the indicated markers, HLA-DR (FIG. 1A), CD83 (FIG. 1B), CXCR4 (FIG. 1C), CCR7 (FIG. 1D), CD80 (FIG. 1E), CD86 (FIG. 1F), MR (FIG. 1G), and CD32 (FIG. 1H), by staining with PE- or FITC-conjugated mAbs. Isotype controls for direct stains exhibited mean fluorescence <5. Results are expresses as percentage of positive cells (□) and as mean fluorescence intensity (MFI, ■).

FIG. 2 is a graph showing endocytic activity of DCs exposed to c-di-GMP. DCs were left untreated (Untr) or were treated with NaCl, c-di-GMP or LPS for 24 h. Mannose receptor-mediated endocytosis was evaluated as the cellular uptake of FITC-dextran (DX) and measured using FACS. Results are expressed as percentage of positive cells.

FIGS. 3A and 3B are graphs showing the effect of c-di-GMP on cytokine production. Analysis of cytokine supernatant concentration in NaCl (used as control) or c-di-GMP-treated immature (FIG. 3A) or mature (LPS-treated; FIG. 3B) DCs was determined by ELISA. Supernatants were harvested after 24 h of treatment and tested for TNF-α, IL-6, IL-1β, IL-10 and IL-12 Results are expressed as pg/ml. IL-12 concentration was undetectable in immature DC culture supernatants. iDC=immature DC; mDC=mature DC.

DETAILED DESCRIPTION OF THE INVENTION

Figure 1A:
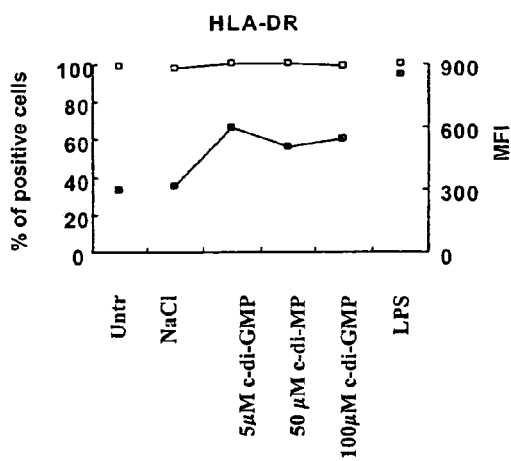

The results shown in the Example presented hereinbelow show that c-di-GMP stimulates and activates DCs, T cells and the Th-1 response, up-regulates the expression of important costimulatory molecules and the proinflammatory response and show that c-di-GMP has neuroactivity and is neuroprotective against nerve damage.

Stimulation or enhancement (immunostimulation) of the immune and inflammatory response can be achieved by exogenous cyclic di-GMP or cyclic dinucleotides and cyclic dinucleotide analogs. Accordingly, cyclic di-GMP and cyclic dinucleotide analogues thereof can also be used in the development of a drug platform technology against a variety of diseases and immunological and inflammatory diseases including but not limited to infectious disease (such as microbial, bacterial, viral, and parasitic infections), cancer, HIV and AIDS, rheumatoid arthritis, and Hodgkin's disease. Cyclic di-GMP and cyclic dinucleotide analogues thereof are also useful as immunotherapeutic agents against cancers and allergic reactions, and as a vaccine adjuvant (e.g. in DNA vaccines, live attenuated vaccines, killed vaccines). Cyclic di-GMP and cyclic dinucleotide analogues thereof are also useful in affecting neuroactivity and in the inhibition or treatment of various brain, nervous and neural disorders.

Several chemotactic cytokines, or chemokines, inhibit HIV replication by blocking or down regulating chemokine receptors that serve as entry cofactors for the virus. The role of chemokine receptors in HIV pathogenesis has been the subject of intense interest.

Cyclic dinucleotides can alter cytokine and chemokine production and therefore activities of their associated receptors. An aspect of the present invention relates to the immunotherapeutic use of cyclic di-GMP or cyclic dinucleotide analogues thereof in the treatment and/or inhibition of diseases such as HIV and AIDS, rheumatoid arthritis, colon cancer, breast cancer, Hodgkin's disease and lymphomas.

The cyclic dinucleotide compounds described herein alter the expression of DCs, T cells, cytokines, chemokines, costimulatory molecules, and nerve cells. The expression or activity of other proteins, including other receptors, may also be altered by the presence of cyclic dinucleotides, such as c-di-GMP, or cyclic dinucleotide analogues of c-di-GMP.

The present invention therefore provides a method for stimulating or enhancing immune or inflammatory response in a patient. This method involves administering to a patient in need thereof an amount of cyclic di-GMP, or a cyclic dinucleotide analogue thereof, effective to stimulate or enhance the immune or inflammatory response in the patient. The immune response stimulated or enhanced in the present invention preferably includes a Th1 oriented immune response.

By stimulating or enhancing immune or inflammatory response, the present invention is able to treat immunological or inflammatory diseases or disorders such as, but not limited to, arthritis, cancer (e.g., breast cancer, colon cancer, lymphomas, etc.) an autoimmune disease or disorder (e.g., rheumatoid arthritis, multiple sclerosis, lupus erythematosus, etc.), an allergic reaction (e.g., asthma, etc.), a chronic infectious disease (e.g., tuberculosis, cryptococal infections, etc.), an infectious disease in which the pathogen or toxin produced impairs the immune response thereto (e.g., anthrax), and an immunodeficiency disease or disorder (e.g., HIV and AIDS, etc.). In the case of anthrax, cyclic di-GMP or a cyclic dinucleotide analogue thereof can be used to stimulate or enhance the immune or inflammatory response which has been impaired or inactivated by the anthrax lethal toxin. Thus, the use of cyclic di-GMP or a cyclic dinucleotide thereof is capable of restoring the function of dendritic cells impaired by the toxin. This use would also restore the patient's capacity to stimulate T cells, to upregulate costimulatory molecules and to produce proinflammatory cytokines that were diminished by the toxin.

Based on the ability of c-di-GMP to directly inhibit cancer cell proliferation (Karaolis et al., 2005), an increased host response in fighting infection as seen by an increased ability of antimicrobial activity in vivo compared to in vitro, as well as its ability to biologically modulate the immunological and inflammatory response, small-molecule cyclic dinucleotides, such as c-di-GMP and cyclic dinucleotide analogues thereof, can be used for immunotherapy and to prevent or treat cancer.

Local immunotherapy relates to treating one part of the body. When body tissues become inflamed, the cells of the immune system become stimulated to fight pathogenic bacteria, viruses and other "foreign" cells. Cancer cells are viewed as foreign cells by the immune system so cyclic dinucleotides can be used for local immunotherapy. In this case, the cancer or tumors might be surgically removed and the cyclic dinucleotide (alone or in combination with other drugs) is administered at the site using a syringe or catheter.

Cyclic di-GMP or a cyclic dinucleotide analogue thereof can also be used clinically for systemic immunotherapy.

The present invention also provides a method for inhibiting, treating, or ameliorating the effects of an injury, disease, disorder or condition that result in neuronal degeneration. The method involves administering to a patient in need thereof an amount of cyclic-di-GMP, or a cyclic dinucleotide analogue thereof, effective to inhibit, treat, or ameliorate the effects of the injury, disease, disorder, or condition that result in neuronal degeneration. Cyclic di-GMP or a cyclic dinucleotide analogue thereof can be used to protect against neuronal damage and degeneration, such as following a primary nervous system injury or as a result of a neurodegenerative disease or disorder. In addition, such cyclic dinucleotides can be used to ameliorate the effects of disease or disorder that result in a degenerative process.

Non-limiting examples of neurodegeneration include degeneration occurring in either gray or white matter (or both) as a result of various diseases or disorders, including diabetic neuropathy, senile dementias, Alzheimer's disease, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia Vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease, lipoproteinemia, etc.

Non-limiting examples of nervous system injury include closed head injuries and blunt trauma, such as those caused by participation in dangerous sports, penetrating trauma, such as gunshot wounds, hemorrhagic stroke, ischemic stroke, glaucoma, cerebral ischemia, damages caused by nerve damaging agents such as toxins, poisons, chemical (biowarfare) agents or damages caused by surgery such as tumor excision.

Bis(3'->5')-cyclic diguanylic acid (c-di-GMP), a cyclic dinucleotide, is the preferred embodiment used in the methods of the present invention. The chemical structure of c-di-GMP is presented below.

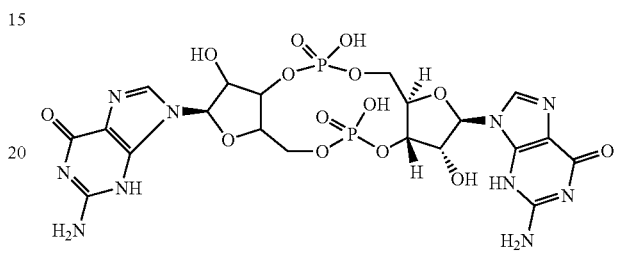

Methods of synthesis of c-di-GMP have been described, for example, by Kawai et al. (Kawai R, Nagata R, Hirata A, Hayakawa Y (2003) A new synthetic approach to cyclic bis (3'->5')diguanylic acid. *Nucleic Acids Res Suppl.* 3:103-4; hereby incorporated by reference herein).

Besides c-di-GMP, a cyclic dinucleotide analogue thereof which acts as a c-di-GMP agonist, i.e., having the same effect as c-di-GMP, can be used. Non-limiting examples of cyclic dinucleotide analogues of c-di-GMP are presented below as compounds (I)-(XX):

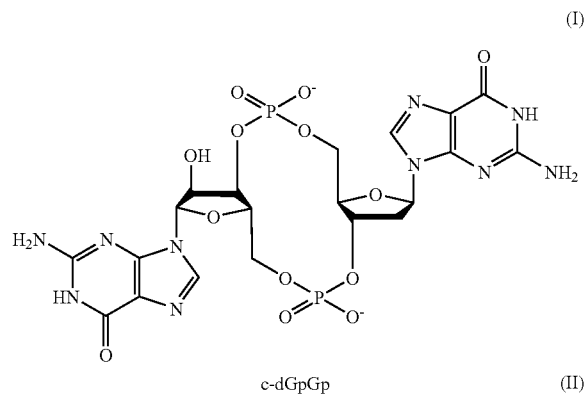

c-dGpGp (I)

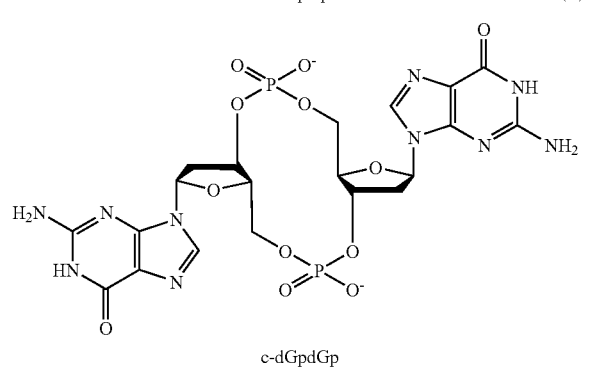

c-dGpdGp (II)

-continued
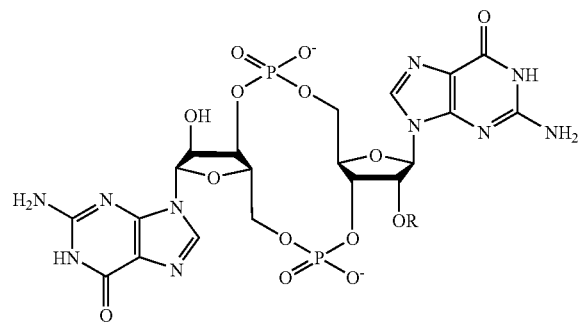
c-G(2'-OR)pGp  
R = CH₃, C₂H₅, etc.
(III)
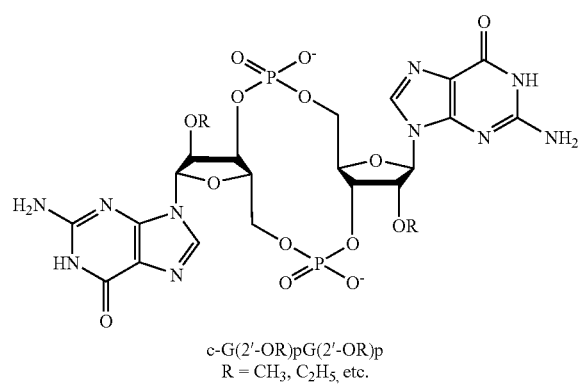
c-G(2'-OR)pG(2'-OR)p  
R = CH₃, C₂H₅, etc.
(IV)
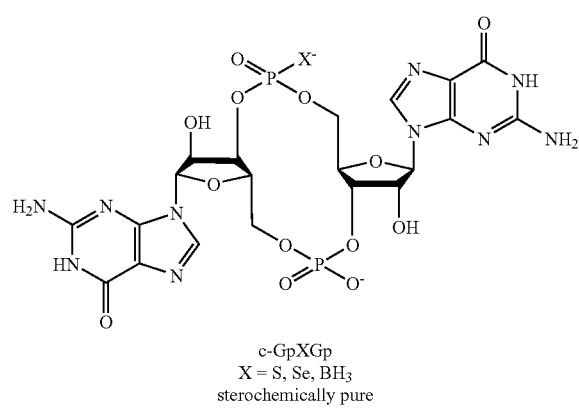
c-GpXGp  
X = S, Se, BH₃  
sterochemically pure
(V)
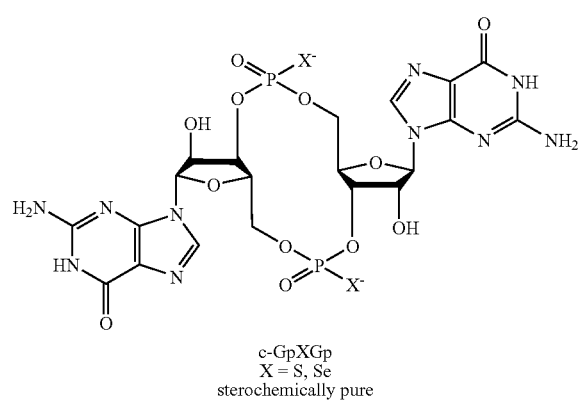
c-GpXGp  
X = S, Se  
sterochemically pure
(VI)

-continued
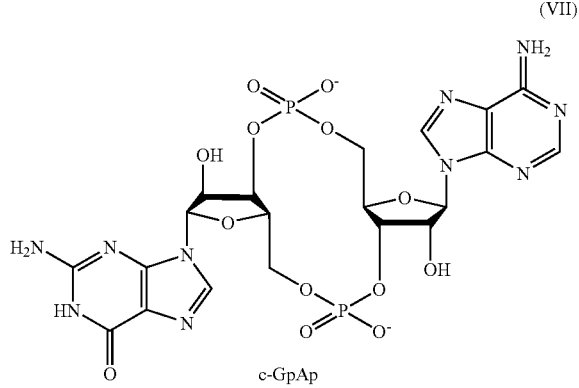
c-GpAp (VII)
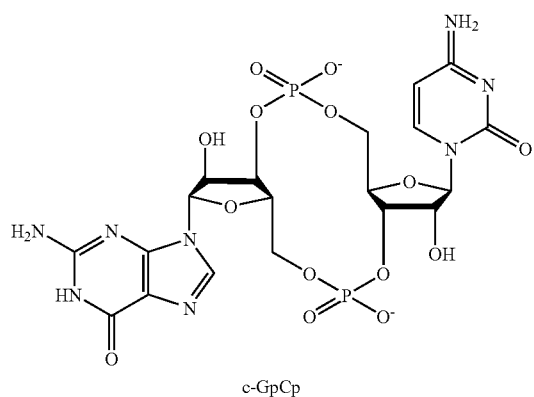
c-GpCp (VIII)
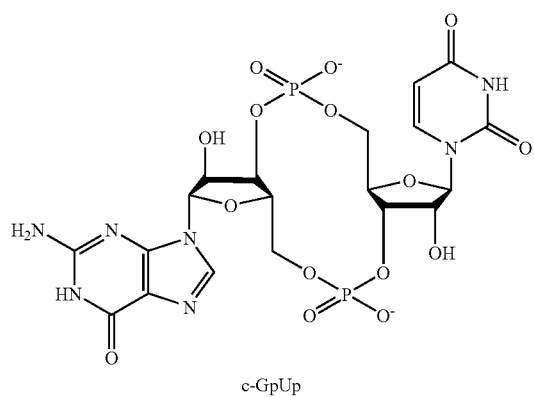
c-GpUp (IX)
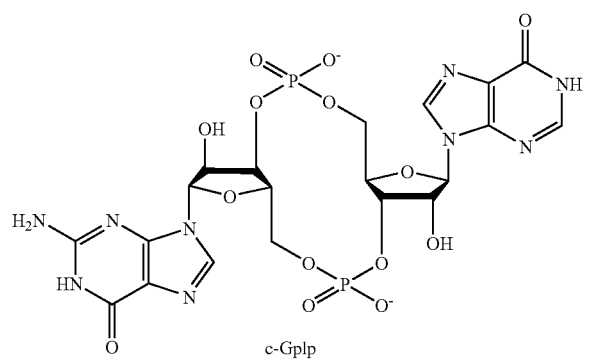
c-GpIp (X)

-continued
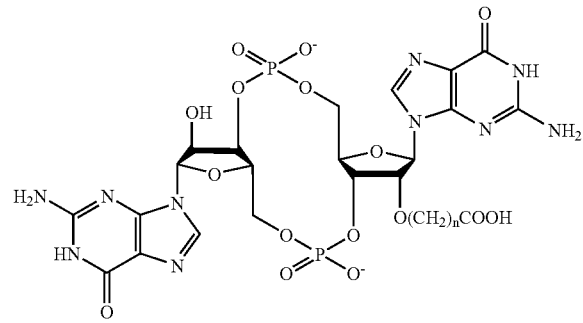
(XI)
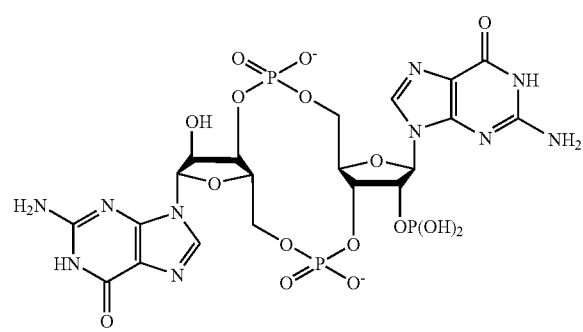
(XII)
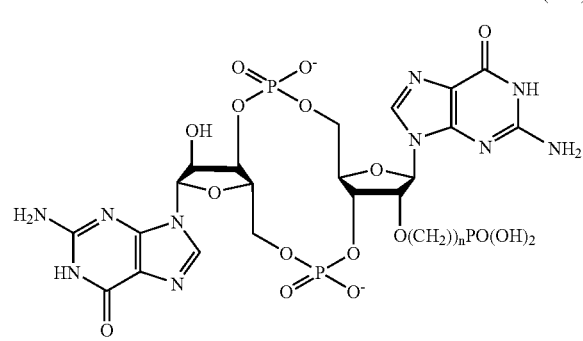
(XIII)
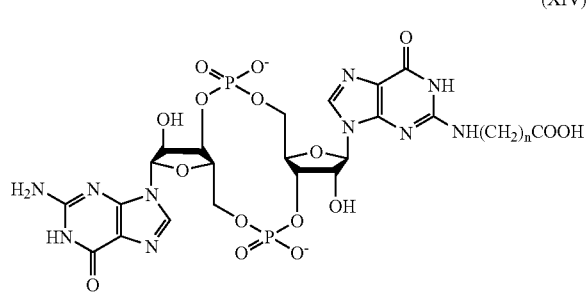
(XIV)
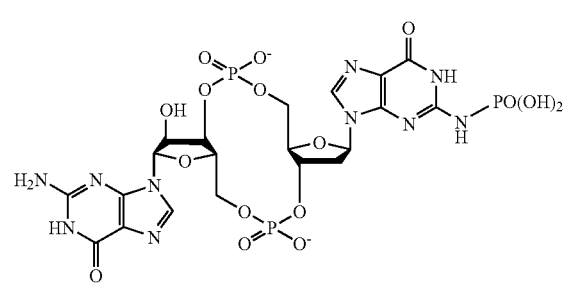
(XV)

-continued
(XVI)
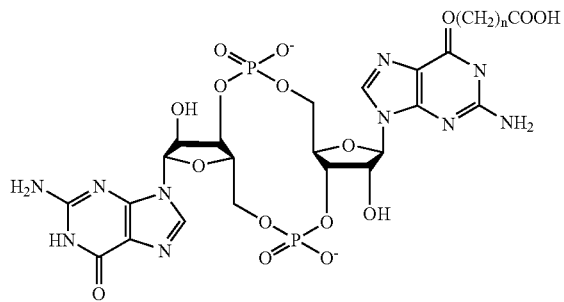
(XVII)
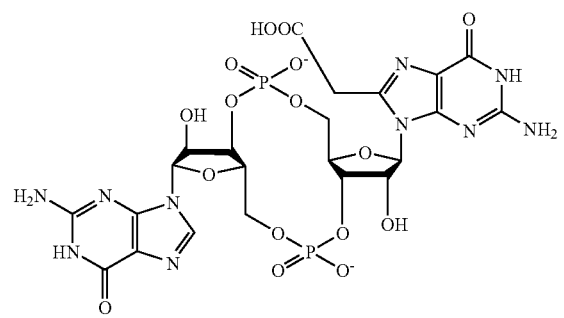
(XVIII)
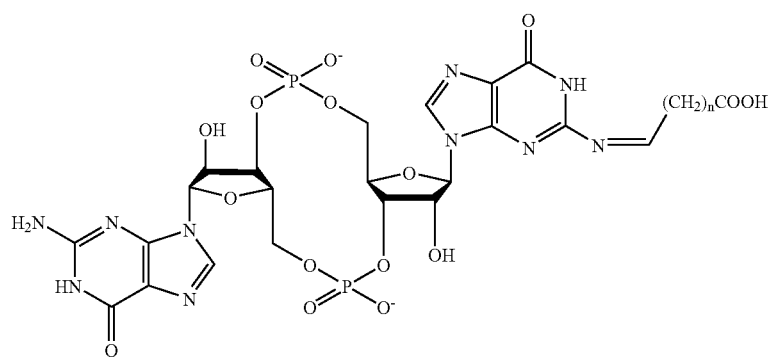
(XIX)
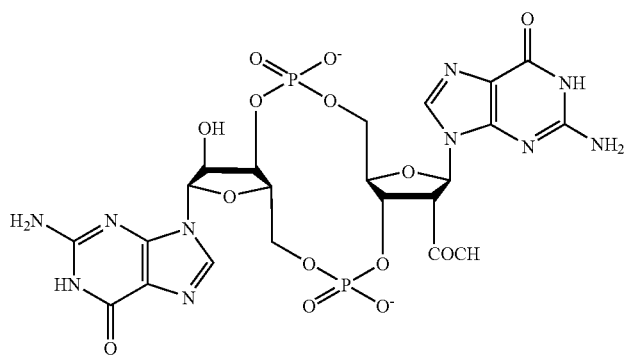

-continued (XX)

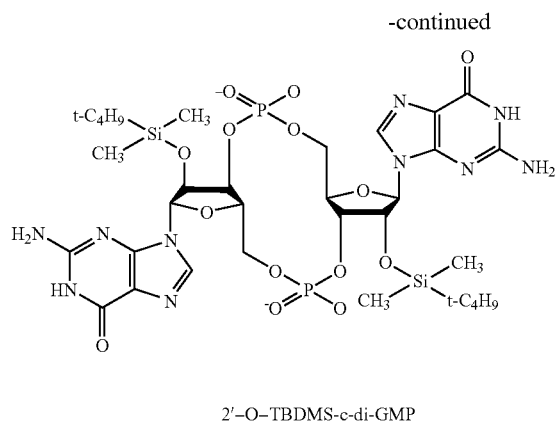

2'-O-TBDMS-c-di-GMP

The above cyclic dinucleotides are only preferred embodiments of the cyclic dinucleotide analogues of c-di-GMP and are not intended to be limiting. For example, the guanine base can be substituted with other bases.

As cyclic dinucleotides may also be modified to yield cyclic dinucleotide analogues, these modified cyclic dinucleotide analogues, and methods of use thereof, are included as aspects of the present invention. c-di-GMP can be modified, for example at a C, N, O, or P, to yield a c-di-GMP analogue. c-di-GMP analogues for use in the present invention have an activity similar to that of c-di-GMP. For example, certain c-di-GMP analogues either increase or reduce the stimulation of DCs and T cells, expression of various cytokines, chemokines, and/or their associated receptors. The degree of reduced expression in the presence of the c-di-GMP analogue may be the same, less, or greater than the degree of reduced expression in the presence of c-di-GMP. Certain c-di-GMP analogues increase expression of certain cytokines. The degree of increased cytokine expression in the presence of the c-di-GMP analogue may be the same, less, or greater than the degree of increased cytokine expression in the presence of c-di-GMP.

A c-di-GMP analogue may be further modified, yielding another c-di-GMP analogue. The further modified c-di-GMP analogues will have properties similar to the original c-di-GMP analogue. These further modifications may result in desired properties, for example, altered toxicity, altered immune or inflammatory response, or uptake into cells.

MeSate-c-di-GMP is a cyclic dinucleotide analogue of cyclic di-GMP which has increased hydrophobicity and lipophilicity over c-di-GMP for increasing cellular uptake and cell-membrane permeability, and therefore, increased bioavailability. Modification of either one or both of the phosphodiester linkage in c-di-GMP by a phosphotriester, which is converted to the phosphodiester would occur via enzymatic cleavage inside the cell. This derivative (analogue) has the negative charge of the phosphate group transitorily masked with carboxyesterase labile S-acyl-2-thioethyl (SATE) groups. Once intracellular, such derivatives are expected to be hydrolyzed in the body to release the parent cyclic dinucleotide molecule. While the present invention relates to the use of cyclic dinucleotides (and not oligonucleotides), MeSate phosphotriester molecules have been synthesized to overcome the hurdle of poor uptake of oligonucleotides (Vives et al., 1999). The synthesized molecules are masked with a carboxyesterase labile S-Acyl-2-thioethyl (SATE) group to gain more lipophilicity. This SATE group effectively crosses the cell membrane. Particular oligonucleotide molecules bearing the enzymolabile SATE groups with acyl equal to acetyl were named MeSATE prooligos. MeSATE nucleoside monophosphates have also been synthesized (Peyrottes et al., 2004).

2'-O-TBDMS-c-di-GMP is a 2'-O-blocked derivative (analogue) of cyclic di-GMP that is expected to have similar chemical properties to those of natural c-di-GMP, but is also expected to have higher cell-membrane permeability than that of natural c-di-GMP. 2'-O-monopyrenylmethyl-c-di-GMP (fluorescently labeled) and 8-monotritium-labeled c-di-GMP (radioactively labeled) can be used for detection assays.

c-di-GMP is well-suited for therapeutic use. It is nontoxic on normal rat kidney cells exposed to 400 µM C-di-GMP for 24 h, and non-lethal in CD1 mice after 24 h when given 50 µl of 200 µM c-di-GMP. c-di-GMP is soluble in water physiological saline, and stable at physiological conditions (pH 10). The structure of the molecule is known, and it is small in size, approx. 700 Da. Analogues can be easily designed and synthesized.

Numerous c-di-GMP analogues can be readily synthesized. A collection of a number of c-di-GMP analogues will be considered to be a library of c-di-GMP analogues. A library of c-di-GMP analogues will be useful in the methods of the present invention. For example, a library of c-di-GMP analogues may be screened to identify a particular c-di-GMP analogue of a desired activity. A particular c-di-GMP analogue may undergo a variety of tests, including testing its ability to stimulate the immune system, testing its effect on DCs, cytokines, testing its ability to affect certain infectious diseases, cancer, immune and inflammatory disorders, testing its use as a vaccine adjuvant, testing its use against allergic reactions and its neuroprotective ability.

Standard techniques such as detection of antibodies to chemokines, protein labeling, binding assays, and functional assays may be used to detect cytokine, chemokine, and receptor expression in a cell.

Pharmaceutical compositions containing at least one of c-di-GMP or a cyclic dinucleotide analogue thereof, or mixtures thereof, for use in accordance with the methods of the present invention may be formulated in conventional manner using one or more physiologically acceptable carriers or excipients. The carrier(s) must be "acceptable" in the sense of being compatible with the other ingredients of the composition and not be deleterious to the recipient thereof. The carrier must be biologically acceptable and inert, i.e., it must permit the cell to conduct its metabolic reactions so that the compound of this invention may effect its inhibitory activity.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results. It will also be appreciated that c-di-GMP or a cyclic dinucleotide thereof may be used alone as the active ingredient or in combination with other active agents.

The term "carrier" refers to a diluent, adjuvant, excipient, or vehicle with which the c-di-GMP or cyclic dinucleotide thereof is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulfate; a glidant, such as colloidal silicon dioxide; a sweetening agent, such as sucrose or saccharin; and/or a flavoring agent, such as peppermint, methyl salicylate, or orange flavoring.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated, i.e., enterically-coated by methods well-known in the art.

Preparations for oral administration may be suitably formulated to give controlled release of the active compound.

For topical administration, c-di-GMP or a cyclic dinucleotide analogue thereof is incorporated into topically applied vehicles such as salves or ointments.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. A nasal spray, which does not require a pressurized pack or nebulizer as in an inhalation spray, can alternatively be used for intranasal administration. In the case of a pressurized aerosol, the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

A typical regimen for treatment includes administration of an effective amount over a period of several days, up to and including between one week and about six months.

In the present application, "patient" will encompass any mammal that requires immunostimulation or immunomodulation, requires prevention of disease, or is suffering from an immune or inflammatory disease involving production of cytokines, chemokines and/or associated receptors.

The effective dose for immunotherapy appears to be in the micromolar range, such as between about 1 $\mu$M and 200 $\mu$M, preferably about 5 $\mu$M to 100 $\mu$M, more preferably about 50 $\mu$M to 100 $\mu$M. The effective dose for protection from neurodegeneration (i.e., neuroprotection) is in a range of about 0.1 to 100 $\mu$M, preferably about 1 to 50 $\mu$M, more preferably aout 1 to 10 $\mu$M. It is within the skill of those in the pharmaceutical art to determine with routine experimentation what dosage of c-di-GMP or a cyclic dinucleotide analogue thereof will be needed, depending on route of administration, to deliver such an effective dose. The desired dose may be administered as 1 to 6 or more subdoses administered at appropriate intervals as required. The compounds may be administered repeatedly, or may be slowly and constantly infused to the patient. Higher and lower doses may also be administered.

It is understood that the dosage of c-di-GMP or a cyclic dinucleotide analogue thereof administered in vivo may be dependent upon the age, sex, health, and weight of the recipient, kind of concurrent treatment, if any, frequency of treatment, and the nature of the pharmaceutical effect desired. The ranges of effective doses provided herein are not intended to be limiting and represent preferred dose ranges. However, the most preferred dosage may be tailored to the individual subject, as is understood and determinable by one skilled in the relevant arts. See, e.g., Berkow et al., eds., *The Merck Manual*, 16$^{th}$ edition, Merck and co., Rahway, N.J., 1992; Goodman et al., eds., *Goodman and Gilman's The Pharmacological Basis of Therapeutics*, 8$^{th}$ edition, Pergamon Press, Inc., Elmsford, N.Y. (1990); Katzung, *Basic and Clinical Pharamacology*, Appleton and Lange, Norwalk, Conn., (1992); *Avery's Drug Treatment: Principles and Practic of Clinical Pharmacology and Therapeutics*, 3$^{rd}$ edition, ADIS Press, LTD., Williams and Wilkins, Baltimore, Md. (1987), Ebadi, *Pharmacology*, Little, Brown and Col, Boston, (1985), *Remington's Pharmaceutical Sciences*, seventeenth edition, ed. Alfonso R. Gennaro, Mack Publishing Company, Easton, Pa. (1985) which references are entirely incorporated herein by reference.

The methods of the present invention may be practiced by administration of cyclic di-GMP or cyclic dinucleotide analogues thereof by themselves or in a combination with other active ingredients, including antiviral compounds and/or antibiotic agents in a pharmaceutical composition. Other active agents suitable for use herein are any compatible drugs that are effective by the same or other mechanisms for the intended purpose, or drugs that are complementary to those of the present agents. These include agents that are effective antibiotic agents.

Cyclic di-GMP or a cyclic dinucleotide thereof may be used in vaccine formulations as an adjuvant in order to boost, stimulate or modulate the immune response. Thus, one aspect of the method for stimulating or enhancing immune or inflammatory response according to the present invention is to enhance the immune response to a vaccine where an effective amount of a vaccine or antigen is administered to the patient in need thereof in combination with an amount of cyclic di-GMP or a cyclic dinucleotide analogue thereof effective to enhance the patient's immune response to the vaccine.

Antigens administered to a patient with cyclic di-GMP or a cyclic analogue thereof as adjuvant include purified or partially-purified preparations of protein, peptide, carbohydrate or lipid antigens, and/or antigens associated with whole cells, particularly dendritic cells that have been mixed with the antigen. On the whole, any pathogen or tumor and/or differentiation associated antigen can be considered as a possible immunogen to be given at the same time as cyclic di-GMP, or a cyclic dinucldotide analogue thereof, as adjuvant.

It is fully expected that the present invention will enhance the immune response to the administration of any vaccine, including a protein vaccine, a polysaccharide vaccine, a DNA vaccine, a killed or live attenuated bacterial or viral vaccine, an autologous or allogeneic cancer vaccine, a dendritic or T cell vaccine, etc. While the term "vaccine" is often used to refer only to vaccinations intended to induce prophylaxis, the term as used throughout the present specification and claims is intended to include vaccination for therapeutic purposes as well. For example, vaccines that comprise tumor-associated antigens are intended to induce an immune response against tumors. Vaccines to viral particles may be used not only to create prophylaxis against the virus, but also to eradicate an existing viral infection. Thus, for example, vaccines are available against HBV and others against AIDS and HCV, which are in active development. Active vaccination against amyloid-β plaques is also in development for the treatment of Alzheimer's disease. Thus, the term "vaccine" applies to the administration of any antigen for the purpose of inducing an immune response against that antigen or to a cross-reactive antigen that exists in situ. Preferred vaccines include an influenza, smallpox, anthrax, hepatitis B virus, human pappilloma virus, herpes simplex virus, polio, tuberculosis or anti-cancer vaccine.

The amount of antigen(s) present in each vaccine dose, is selected as an amount capable of inducing a protective immune response in vaccinated subjects. This amount will depend on the specific antigen and the possible presence of typical adjuvants, and can be identified by a person skilled in the art. In general, each dose will contain 1-1000 micrograms of antigen, preferentially 10-200 µg. Further components can be also present advantageously in the vaccine. The effective amount of cyclic di-GMP or a cyclic dinucleotide analogue thereof as adjuvant in an immunizing composition is in a range of about 1 to 200 µM, preferably about 5 to 100 µM, more preferably about 50 to 100 µM.

The vaccine composition can be formulated in-any conventional manner, as a pharmaceutical composition comprising sterile physiologically compatible carriers such as saline solution, excipients, adjuvants (if any, in addition to the cyclic di-GMP or a cyclic dinucleotide analogue thereof), preservatives, stabilizers, etc.

The vaccine can be in a liquid or in lyophilized form, for dissolution in a sterile carrier prior to use. The presence of alum or liposome-like particles in the formulation are also possible, since they are useful for obtaining a slow release of the antigen(s). Other strategies for allowing a slow release of the vaccine can be easily identified by those skilled in the art and are included in the scope of this invention.

The pharmaceutically acceptable carrier, excipient, diluent or auxiliary agent can be easily identified accordingly for each formulation by a person skilled in the art.

This method of the present invention can be used in both prophylactic and therapeutic treatment of infectious diseases and cancer. In particular, the method can be used in a treatment for preventing viral and bacterial diseases (i.e., prophylactic vaccines) as well as for the treatment of severe chronic infection diseases (i.e., therapeutic vaccines). Moreover, the method can also be used in the prevention/inhibition and treatment of cancer or other diseases and conditions when suitable antigens are used.

This can be achieved by using antigens against infectious agents associated with human malignancies, e.g., EBV, HPV and H. pilori, or well defined tumor associated antigens such as those characterized in human melanoma, e.g., MAGE antigens, thyrosinase gap100, and MART, as well as in other human tumors.

Also encompassed by the present invention, as will be appreciated by those of skill in the art, is a method for stimulating or enhancing an immune response in a patient by activating dendritic cells or T cells (either autologous or allogeneic) ex vivo with an effective amount of antigen and with an effective amount of cyclic di-GMP or a cyclic dinucleotide thereof prior to administering the activated dendritic cells or T cells as a cellular vaccine to a patient.

Having now generally described the invention, the same will be more readily understood through reference to the following example which is provided by way of illustration and is not intended to be limiting of the present invention.

EXAMPLE

Preparation of Cell Culture and Treatments

Peripheral blood mononuclear cells (PBMC) were isolated by Ficoll-Hypaque gradient separation of buffy coats obtained from healthy volunteer blood donors by the Transfusion Center of Universita Degli Studi "La Sapienza" Rome. DCs were generated from monocytes purified from PBMC by positive selection using magnetic cell separation columns and CD14 Microbeads. Highly enriched monocytes (>95% CD14$^+$) were cultured at 6×10$^5$/ml in RPMI 1640 medium supplemented with 15% heat-inactivated fetal calf serum (FCS), L-glutamine and penicillin-streptomycin and 250 ng/ml granulocyte macrophage-colony stimulating factor (GM-CSF) and 500 U/ml interleukin (IL)-4 at 37° C. for 5 days. Differentiation to DC was assessed both by morphologic observation and the detection of specific surface markers by flow cytometry. These cells were CD14$^-$, CD1a$^+$, HLA-DR$^{intermediate}$, HLA-ABC$^{intermediate}$, CD80$^{low}$, CD86$^{low}$ consistent with an immature DC phenotype.

Untreated immature DCs were used as controls. After 5 days of culture c-di-GMP and/or 200 ng/ml lipopolysaccharide (LPS) (*Escherichia coli* serotype 0111:B4) were added to immature DCs. LPS-treated DCs became stimulated/activated and produced CD83$^+$, HLA-DR$^{high}$, HLA-ABC$^{high}$ consistent with a mature DC phenotype.

A dose-response titration curve using 0.5, 5, 50, 100 and 200 uM c-di-GMP was performed. No effect was obtained using 0.5 µM c-di-GMP, and 200 µM gave inconsistent results. Only experiments performed using c-di-GMP at the concentration of 5, 50 and 100 µM are reported. Experiments using trypan blue exclusion tests were always performed in order to exclude any aspecific toxicity of c-di-GMP. NaCl (0.9%) used to resuspend the compound was always included as control.

c-di-GMP Stimulates and Activates Human Dendritic Cells

Cell staining was performed using mouse monoclonal antibodies FITC- or PE-conjugate. The following mAbs were used: CD14 (IgG1, PE), CD1a (IgG1, FITC), HLA-DR (IgG2a, FITC), HLA-ABC (IgG1, FITC), CD80 (IgG1, FITC), CD86 (IgG1, FITC); CD83 (IgG2b, PE), CXCR4 (IgG2aPE), CCR5 (IgG2a, FITC), CD32 (IgG2b, FITC). CD40, CCR7 and mannose receptor (MR) staining was performed using mouse mAb followed by FITC-conjugated affinity purified, isotype-specific goat anti-mouse Abs. Samples were analyzed using a FACScan flow cytometer and CellQuest software (Becton Dickinson). To investigate whether c-di-GMP induced phenotypic differentiation of human DCs, immature and mature DCs were cultured with c-di-GMP for 24 h and then analysed for surface molecule expression.

Figure 1B:
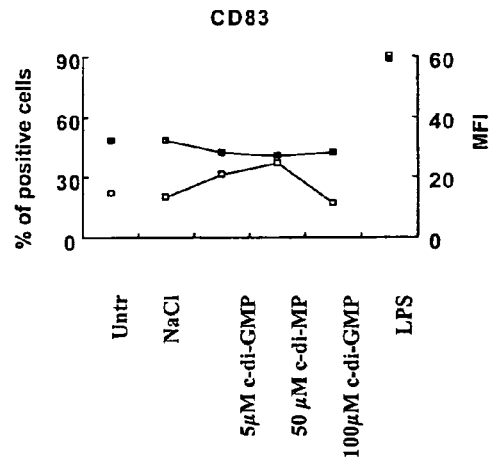
Figure 1C:
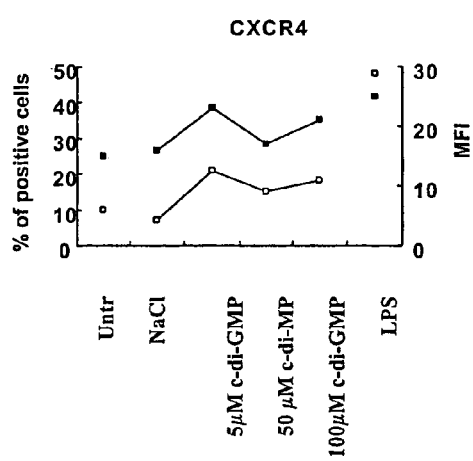
Figure 1D:
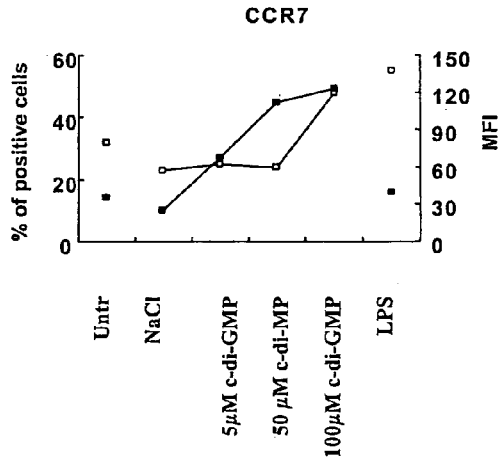
Figure 1E:
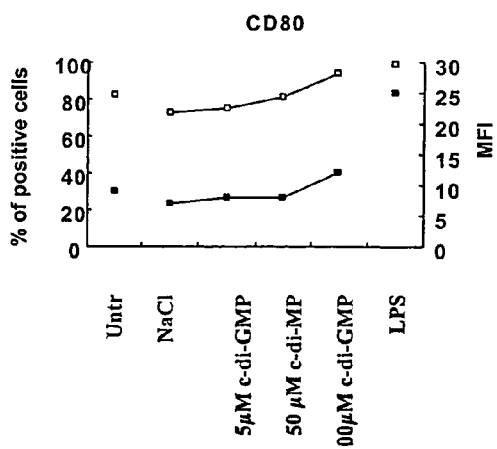
Figure 1F:
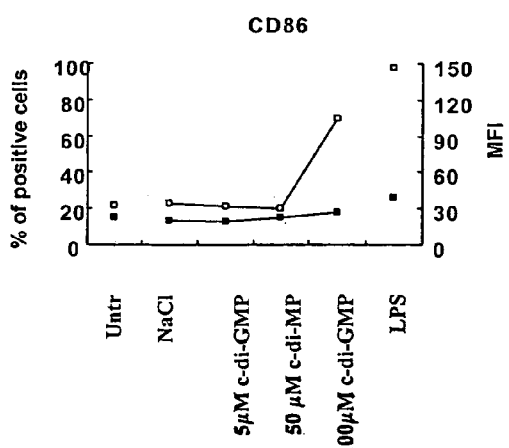

The results indicate that c-di-GMP stimulates immature DCs. In FIG. 1A, c-di-GMP up-regulated the expression of DC antigen-presenting cell MHC associated HLA-DR as seen by an increase in mean fluorescence intensity (MFI), and resulted in a high percentage of positive (expressing) cells similar to the result of LPS treatment. HLA-DR is an important molecule involved in the presentation of antigenic peptides to CD4$^+$T cells. C-di-GMP significantly increased the expression of the chemokine receptors CXCR4 and CCR7 (as seen by a dramatic increase in both mean fluorescence and percentage of expressing cells in FIGS. 1C and 1D). These important chemokine receptors are known to be involved in the migration of mature DC towards lymph nodes. CXCR4 expressing cells are attracted to sites of inflammation and CCR7 is a marker of DCs so these findings suggest an increase in the proinflammatory response and the attraction of these cells to sites of inflammation. C-di-GMP slightly up-regulated the expression of CD83 in a dose-dependent manner (as seen by mean fluorescence of positive cells) with overstimulation resulting in no effect seen at high concentrations (FIG. 1B). CD83 is a maturation antigen. In FIG. 1F, c-di-GMP also up-regulated and stimulated DC antigen-presenting cell costimulatory molecule CD86 (B7-2) (as seen by an increase in the percentage of positive cells). C-di-GMP slightly increased the expression of the costimulatory molecule CD80 (B7-1) (as seen by mean fluorescence and the percentage of expressing cells) in a dose-dependent manner (FIG. 1E). In FIG. 1G, c-di-GMP reduced the expression of mannose receptor (MR) in a dose-dependent manner (as seen by mean fluorescence).

To determine whether the treatment of DCs with c-di-GMP modulates the expression of cell surface molecules that contribute to antigen uptake, the expression of MR and CD32 was tested. At the highest dose, c-di-GMP, similarly to LPS, but to a lower extent, down-regulated MR molecules on the surface of immature DCs (FIG. 1G), while CD32 expression was not affected (FIG. 1H). c-di-GMP did not interfere with LPS-induced maturation (data not shown). As c-di-GMP clearly has an activating effect on immature DC, it appears not to be able to up-regulate surface expression of markers that are already highly expressed on LPS-matured DC. Interestingly, c-di-GMP did not affect surface expression of CD1a and HLA-ABC, involved in the presentation of lipidic and antigenic peptides respectively; CCR5, a chemokine receptor involved in the migration of immature DC in inflamed tissue; and CD40, which transduces activation signals (data not shown).

Taken together, these data suggest that T cells are being activated by c-di-GMP. The results show that iDCs are being activated/matured by c-di-GMP. The results show that the costimulatory molecules CD80 and CD86 are up-regulated by c-di-GMP treatment. The finding that CD83 is not significantly affected (in contrast to LPS which affects most cells and molecules) suggests that c-di-GMP has the advantage of specificity and does not have a general effect on all cells of the immune response. The findings clearly indicate the stimulation of antigen-presenting cells and antigen-specific receptors such as signal 1 MHC factors (e.g., HLA-DR) and signal 2 costimulatory molecules (CD86 and CD80).

c-di-GMP does not Modulate DC Endocytic Activity

Mannose receptor (MR)-mediated endocytosis was measured as the cellular uptake of FITC-dextran (DX) and quantified by flow cytometry. A total of $2 \times 10^5$ cells per sample were incubated in media containing FITC-DX (1 mg/ml) (Mv 40,000). After 15 min of incubation at 37° C. or 4° C. (as negative control), cells were washed four times with cold PBS containing 1%FCS and 0.01%NaN3 and fixed in 1% formaldehyde. The background (cells pulsed at 4° C.) was always subtracted. As shown in FIG. 2, c-di-GMP did not induce any major effect. As expected, LPS down-regulated the uptake of FITC-DX, consistent with a mature phenotype.

c-di-GMP Stimulates/Up-Regulates Cytokine Production by Dendritic Cells

Analysis of supernatant cytokine content was performed both on treated (c-di-GMP) or untreated saline control (NaCl) immature DCs (iDC) and mature DCs (mDC). Culture supernatants were collected after 24 h treatment and IL-1β, IL-6, IL-10, IL-12, and TNF-α contents were measured using a sandwich ELISA according to the manufacturer's instructions.

The results clearly indicated that c-di-GMP stimulates cytokine production in both iDCs and mDCs and clearly show that iMCs are being activated/matured by c-di-GMP (FIG. 3A). In iDCs, a 5 µM dose of c-di-GMP triggered a dramatic increase in the production of TNF-α, demonstrating an increase in the production of proinflammatory molecules. C-di-GMP induced an increase in IL-6 in mDCs at 100 µM and a major increase in IL-1β in mDCs, supporting the induction of a proinflammatory response (FIG. 3B). IL-12 is a central cytokine in the Th-1 response whose expression leads to IFN-γ production. IL-12 secretion was undetectable in immature DCs; however, c-di-GMP induced a dramatic increase in IL-12 production in mDCs at 50 µM. The increase in IL-12 further confirms and is consistent with immunostimulation and the induction of a proinflammatory response, particularly a Th-1 response. There was no major effect on IL-10 expression which is an anti-inflammatory molecule. This data is again consistent with the previous data that c-di-GMP treatment is immunostimulatory and induces a proinflammatory response and therefore can be used in various clinically therapeutic applications such as an immunotherapeutic agent or adjuvant in vaccine development.

c-di-GMP Up-Regulates the Immunostimulatory Capacity of Dendritic Cells

DCs were stimulated for 24 h with c-di-GMP or LPS and were then extensively washed and suspended in RPMI 1640 supplemented with 10% human serum, L-glutamine, and penicillin/streptomicin, irradiated (3,000 rad from a $^{137}$Cs source) and added in graded doses to $1 \times 10^5$ responder T cells in 96 flat-bottom microplates. Responder cells were autologous or allogeneic PBMC. After 5 days, cultures were pulsed for 18 h with 0.5☐Ci/well of [$^3$H]thymidine. Cells were then harvested onto glass fiber filters, and [$^3$H]thymidine incorporation was measured by liquid scintillation spectroscopy.

Figure 4A:
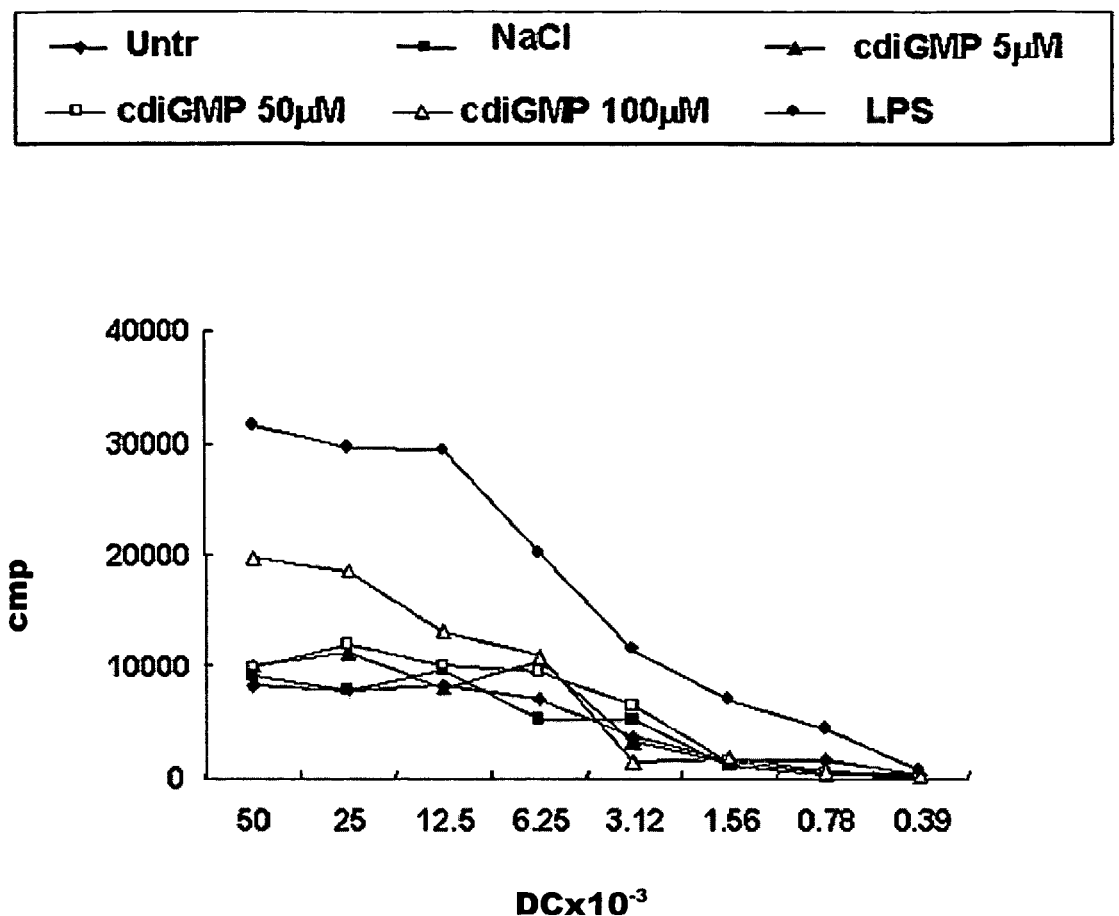
FIGS. 4A and 4B are graphs showing stimulation of autologous and allogeneic PBMC. DCs were left untreated (Untr) or were treated with NaCl, c-di-GMP or LPS for 24 h. A mixed leukocyte reaction, with irradiated DCs cultured at different cell numbers with $1 \times 10^5$ autologous (FIG. 4A) or allogeneic (FIG. 4B) PBMC, was then set up. [$H^3$] thymidine incorporation was measured after 5 days. Results are expressed as count per minutes (cpm).
Figure 4B:
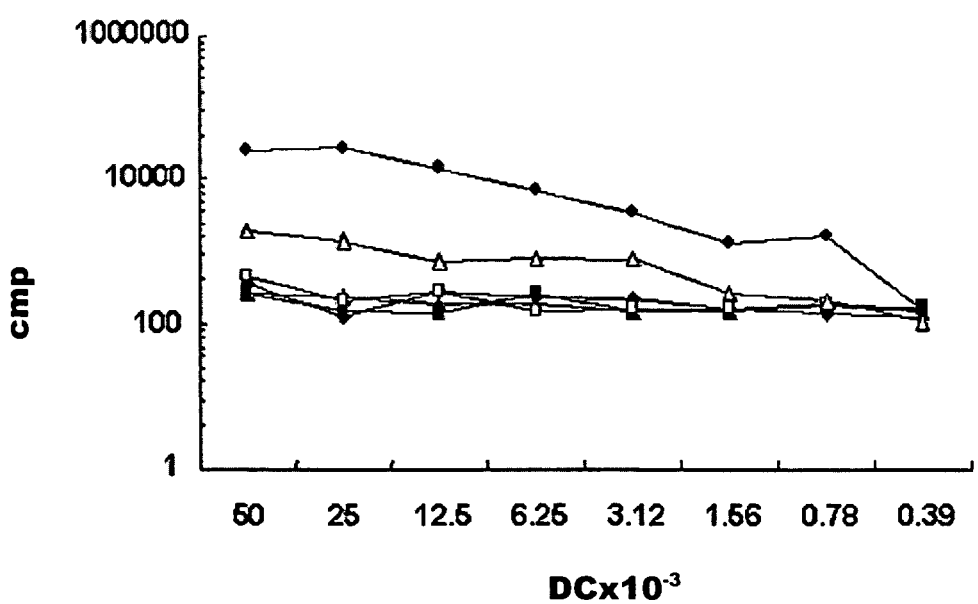

If DCs are activated and if proinflammatory cytokines are stimulated, then T cells are activated. If irradiated (i.e., dead) DCs are mixed with normal T cells, the proliferation of DCs is not expected; however, the proliferation of T cells is expected. Therefore, in this experiment, thymidine incorporation indicates the stimulation of T cells. The results in FIGS. 4A and 4B, demonstrating the proliferation of DCs, indicate that c-di-GMP treatment activates T cells. The results show that if cells are treated with LPS, T cells are highly activated consistent with its known T cell stimulatory activity. The results also show the ability of 100 µM c-di-GMP-treated immature DCs to induce both autologous (FIG. 4A) and heterologous (FIG. 4B) T cell proliferation compared to untreated DCs (five-fold and two-fold increase respectively). Taken together, and consistent with previous data, these results show that c-di-GMP treatment up-regulates and activates/stimulates the proliferation of T cells, further demonstrating that c-di-GMP is an innate stimulator and can be used clinically in immunotherapeutic applications.

c-di-GMP does not Modulate Dendritic Cell Apoptosis

FITC-Annexin V/Propidium Iodure (PI) double staining was used to detect apoptosis of DCs treated with c-di-GMP. Immature and mature DCs, untreated or treated with c-di-GMP for 24 h, were harvested and washed twice with ice cold PBS; specific binding of FITC-annexin V and staining with PI was performed with an apoptosis detection kit accordingly to the manufacturer's instructions. The cells were then analysed by flow cytometry.

As shown in Table 1, c-di-GMP did not appear to have any effect on DC apoptosis. c-di-GMP did not modulate the percentage of annexin V$^+$/PI$^-$ (early apoptosis) and annexin V$^+$/PI$^+$ DCs (late apoptosis) after 24 h treatment. These results indicate a lack of an anti-inflammatory response and that there is no tolerance of DCs to c-di-GMP. These data are consistent with earlier data that show that c-di-GMP is clearly an immunostimulatory molecule and activates the proinflammatory response.

TABLE 1

|  | Early apoptosis (% of annexin V$^+$/PI$^-$ cells) | Late apoptosis (% of annexin V$^+$/PI$^+$ cells) |
| --- | --- | --- |
| Untreated | 29 | 56 |
| NaCl | 22 | 39 |
| cdiGMP 5 µM | 23 | 36 |
| cdiGMP 50 µM | 31 | 40 |
| cdiGMP 100 µM | 18 | 42 |
| LPS | 21 | 52 |
| LPS + NaCl | 28 | 38 |
| LPS + cdiGMP 5 µM | 32 | 33 |
| LPS + cdiGMP 50 µM | 31 | 46 |
| LPS + cdiGMP 100 µM | 29 | 47 | c-di-GMP has Desired Immunotherapy and Adjuvant Properties

The data obtained showing treatment with c-di-GMP is immunostimulatory, triggers a Th-1 response and induces a proinflammatory response, is clearly consistent with an increase in the host response in fighting infection in vivo. This cellular data is consistent with in vivo data from the laboratory of the present inventor showing that c-di-GMP attenuates virulence and inhibits bacterial infection in an animal model of infection. Cyclic dinucleotides such as c-di-GMP stimulate vertebrate immature immune cells to induce maturation and to produce various factors including TNF-α as well as Th-1 cytokines such as IL-12. Therefore, c-di-GMP functions as an adjuvant for regulating the initiation of the Th-1 response and has clinical utility in vaccine development.

Regarding its use as an adjuvant, the data overall also strongly indicate that if administered with an antigen, there is increased presentation of antigen through stimulation of HLA-DR. Cyclic di-GMP facilitates and induces costimulation via an increase in CD80 and CD86, facilitates activation of a Th-1 immune response as seen by the induction of IL-12, facilitates the stimulation of an overall proinflammatory pattern as seen by the increase in IL-1β and TNF-α and facilitates the stimulation of T cells as seen by the data in the mixed leukocyte reaction. C-di-GMP treatment, however, does not appear to stimulate CD83, which is desirable, as this suggests a degree of selectivity for DCs compared to LPS which is broadly hyperstimulatory and results in hyperreactions.

c-di-GMP has Neuroprotective Properties

To assess the role of cyclic dinucleotides in modulating the neurological response, i.e., prevent cell death induced by staurosporine (STS) in primary hippocampal nerve cells, the effects of c-di-GMP on hippocampal cells was analyzed. Primary hippocampal cells were prepared according to previously described methods (Pereira et al., 1993). Briefly, the hippocampi were dissected from the brain of 18-day-old fetal rats. Following enzymatic and mechanical dissociation, cells were plated at a density of 100,000 cells/well in 96-well plates pre-coated with matrigel. At the 7$^{th}$ day after plating, cultures were subjected to one of the following treatments: (i) vehicle (24 h), (ii) STS (100 nM, 22 h), (iii) c-di-GMP (24 h), (iv) c-di-GMP (2 h) followed by c-di-GMP -plus-STS (22 h), (v) c-di-GMP -plus-STS (24 h), or (vi) STS (2 h) followed by c-di-GMP -plus-STS (22 h). At the end of the treatments, cell viability was analyzed using CellTiter 96® AQ$_{ueous}$ Assay (Promega). The assay involves the spectrophotometric measurement (at 490 nm) of the mitochondrial conversion of a tetrazolium dye into a colorful product. The absorbance of the assay correlates with the number of metabolically active cells.

Figure 5:
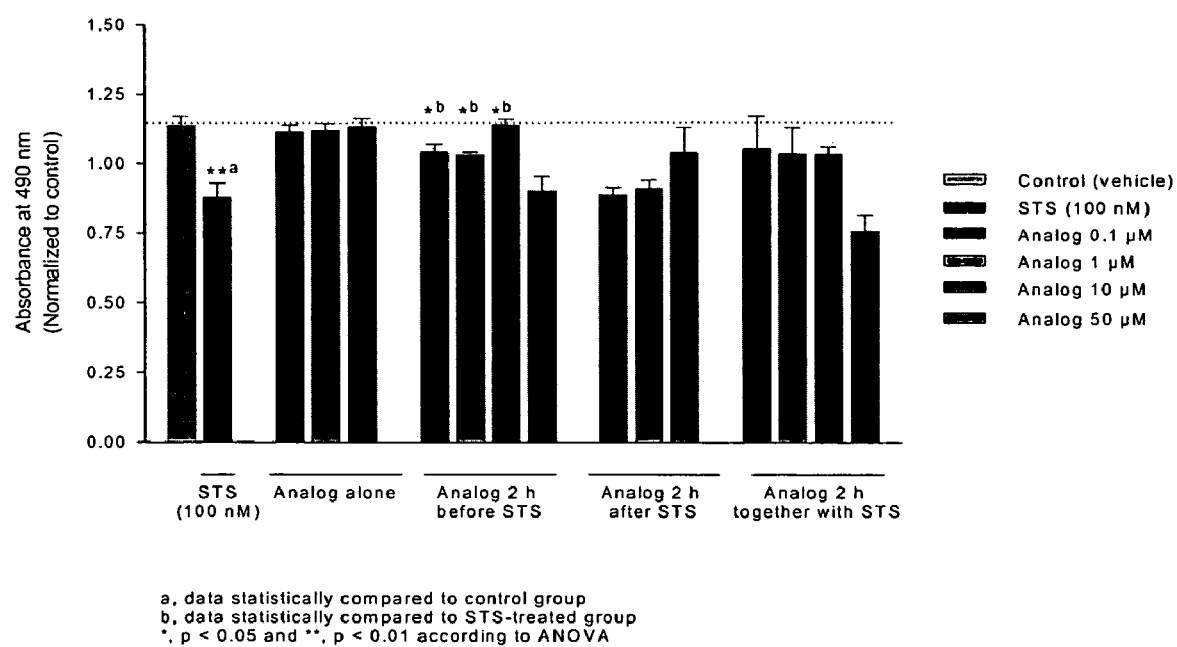
FIG. 5 is a graph showing neuroprotective activity of c-di-GMP on hippocampal cells, protecting cells from both pretreatment and post-treatment damage by the nerve-damaging agent staurosporine.

The results obtained suggest that hippocampal cells are sensitive to c-di-GMP. Treatment of the primary cultures with STS caused significant cell death as expected. c-di-GMP was not toxic to the primary hippocampal cultures. Pre-treatment of the cultures with c-di-GMP (0.1-10 µM) prevented the STS-induced cell death (FIG. 5, where c-di-GMP is referred to as "Analog" in the figure). When c-di-GMP (0.1-10 µM) was applied to the cultures together with or after STS, the number of metabolic active cells was on average higher than that observed in cultures treated with STS alone.

The results show that the c-di-GMP has neuroprotective properties. A concentration of 0.1-10 µM protects hippocampal neuronal cells from damage by staurosporin, a nerve-damaging agent. More importantly, c-di-GMP shows striking neuroprotective activity post-treatment and appears to restore damaged or dying nerve cells to control levels. Using this molecule alone or in combination with other compounds or as part of a vaccine, it is expected that the protective immune response in acute and chronic insults of mechanical or biochemical origin can be safely boosted. Since this molecule is effective even when given after the insult, and because it protects against the toxicity of staurosporine (a very common mediator of secondary degeneration), it can be used clinically to inhibit or treat diseases such as (but not limited to) neurological, brain, or chronic neurodegenerative disorders such as stroke, glaucoma, Alzheimer's disease, Parkinson's disease, and amyotrophic lateral sclerosis.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Agrawal A, Lingappa J, Leppla S H, Agrawal S, Jabbar A, Quinn C, Pulendran B. 2003. Impairment of dendritic cells and adaptive immunity by anthrax lethal toxin. *Nature*. 2003 Jul. 17, 2003; 424(6946):329-34.

Asadullah K, Volk H D, Friedrich M, Sterry W. 2002. Experimental therapies for psoriasis. *Arch Immunol Ther Exp* (Warsz). 50(6):411-20.

Banchereau, J, and Steinman, R. M. 1998. Dendritic cells and the control of immunity. *Nature* 392:245-252.

Bazan et al, "Mediators of injury in neurotrauma: intracellular signal transduction and gene expression", *J. Neurotrauma* 12(5):791-814 (1995)

Ben-Nun et al, "The rapid isolation of clonable antigen-specific T lymphocyte lines capable of mediating autoimmune encephalomyelitis", *Eur. J. Immunol.* 11(3):195-199 (1981a)

Boyaka P N, McGhee J R. 2001. Cytokines as adjuvants for the induction of mucosal immunity. *Adv Drug Deliv Rev.* September 23; 51(1-3):71-9.

Bradney C P, Sempowski G D, Liao H X, Haynes BF, Staats H F. 2002. Cytokines as adjuvants for the induction of anti-human immunodeficiency virus peptide immunoglobulin G (IgG) and IgA antibodies in serum and mucosal secretions after nasal immunization. *J Virol.* 2002 January; 76(2):517-24.

Brauner-Osborne et al, "A new structural class of subtype-selective inhibitor of cloned excitatory amino acid transporter, EAAT2" *Eur J Pharmacol,* 406:41-44 (2000)

Brenneman D E, Hauser J, Spong C Y, Phillips T M, Pert C B, Ruff M. 1999. VIP and D-ala-peptide T-amide release chemokines which prevent HIV-1 GP120-induced neuronal death. *Brain Res.* August 14; 838(1-2):27-36.

Broderson, J. R. 1989. A retrospective review of lesions associated with the use of Freund's adjuvant. *Laboratory Animal Science* 39:400-405.

Buchanan R M, Arulanandam B P, Metzger D W. 1998. IL-12 enhances antibody responses to T-independent polysaccharide vaccines in the absence of T and NK cells. *J Immunol.* November 15; 161(10):5525-33.

Burns et al, "Isolation of myelin basic protein-reactive T-cell lines from normal human blood", *Cell Immunol.* 81(2): 435-440 (1983)

Chapel, H. M. and August, P. J. 1976. Report of nine cases of accidental injury to man with Freund's complete adjuvant. *Clinical and Experimental Immunology* 24:538-541.

Cheminay, C., Mohlenbrink, A., Hensel, M. 2005. Intracellular *salmonella* inhibit antigen presentation by dendritic cells. *J Immunol* 174:2892-9.

Clemons K V, Stevens D A. 2001. Overview of host defense mechanisms in systemic mycoses and the basis for immunotherapy. *Semin Respir Infect.* March; 16(1):60-6.

Dalpke, A., Zimmermann, S. and Heeg, K. 2002. *Biol Chem* 383:1491-500.

Dalpke, A. H., Schafer, M. K., Frey, M., Zimmermann, S., Tebbe, J. Weihe, E. and Heeg, K. 2002. *J Immunol* 168: 4854-63.

Egeter O, Mocikat R, Ghoreschi K, Dieckmann A, Rocken M. 2000. Eradication of disseminated lymphomas with CPG-DNA activated T helper type 1 cells from nontransgenic mice. *Cancer Res.* March 15; 60(6):1515-20.

Faden et al, "Pharmacological strategies in CNS trauma", *Trends Pharmacol. Sci.* 13(1):29-35 (1992)

Faden, A. I., "Experimental neurobiology of central nervous system trauma", *Crit. Rev. Neurobiol.* 7(3-4):175-186 (1993)

Frank, I., Pope, M. 2002. The enigma of dendritic cell-immunodeficiency virus interplay. *Curr. Mol. Med.* 2,229-236

Garbi N, Arnold B, Gordon S, Hammerling G J, Ganss R. 2004. CpG motifs as proinflammatory factors render autochthonous tumors permissive for infiltration and destruction. *J Immunol.* May 15; 172(10):5861-9

Garzino-Demo, A., DeVico, A. L., Conant, K. E. and Gallo, R. C. 2000. The role of chemokines in human immunodeficiency virus infection. *Immunol Rev* 177:79-87.

Gawlick U, Kranz D M, Schepkin V D, Roy E J. 2004. A conjugate of a tumor-targeting ligand and a T cell costimulatory antibody to treat brain tumors. *Bioconjug Chem.* September-October; 15(5):1137-45.

Granucci, F., Vizzardelli, C., Pavelka, N., Feau, S., Persico, M., Virzi, E., Rescigno, M., Moro, G., Ricciardi-Castagnoli, P. 2001. Inducible IL-2 production by dendritic cells revealed by global gene expression analysis. *Nat. Immunol.* 2,882-888.

Hickey, W. F. et al, "T-lymphocyte entry into the central nervous system", *J. Neurosci. Res.* 28(2):254-260 (1991)

Hirschberg et al, "Accumulation of passively transferred primed T cells independently of their antigen specificity following central nervous system trauma" *J. Neuroimmunol.* 89(1-2):88-96 (1998)

Hovda et al, "Diffuse prolonged depression of cerebral oxidative metabolism following concussive brain injury in the rat: a cytochrome oxidase histochemistry study", *Brain Res.* 567(1):1-10 (1991)

Isomura I, Yasuda Y, Tsujimura K, Takahashi T, Tochikubo K, Morita A. 2005. Recombinant cholera toxin B subunit activates dendritic cells and enhances antitumor immunity. *Microbiol Immunol.* 49(1):79-87.

Karaolis, D. K. R., K. Cheng, M. Lipsky, A. Elnabawi, J. Catalano, M. Hyodo, Y. Hayakawa, and J. P. Raufman. 2005. 3',5'-cyclic diguanylic acid (c-di-GMP) inhibits basal and growth factor-stimulated human colon cancer cell proliferation. *Biochem. Biophys. Res. Comm.,* 329:40-45

Kaufman H L, Disis M L. 2004. Immune system versus tumor: shifting the balance in favor of DCs and effective immunity. *J Clin Invest.* March; 113(5):664-7

Kawai R, Nagata R, Hirata A, Hayakawa Y. 2003. A new synthetic approach to cyclic bis(3'→5')diguanylic acid. *Nucleic Acids Res Suppl.* 3:103-4.

Klinman, D. M. 2003. CpG DNA as a vaccine adjuvant. *Expert Rev Vaccines* 2:305-15.

Kramer et al, "Gene transfer through the blood-nerve barrier: NGF-engineered neuritogenic T lymphocytes attenuate experimental autoimmune neuritis", *Nat. Med.* 1(11): 1162-1166 (1995)

Krieg A M. 2002. CpG motifs in bacterial DNA and their immune effects. *Annu Rev Immunol.* 20:709-60.

Lazarov Spiegler et al, "Transplantation of activated macrophages overcomes central nervous system regrowth failure", *FASEB J.* 10(11):1296-1302 (1996)

Lentz, M. R. 1999. The role of therapeutic apheresis in the treatment of cancer: a review. *Ther Apher* 3:40-49.

Lyke, N. 2004. ADP-ribosylating bacterial enzymes for the targeted control of mucosal tolerance and immunity. *Ann N Y Acad Sci* 1029:193-208.

Macpherson G, Milling S, Yrlid U, Cousins L, Turnbull E, Huang F P. 2004. Uptake of antigens from the intestine by dendritic cells. *Ann N Y Acad Sci.* December;1029:75-82.

Martin et al, "Fine specificity and HLA restriction of myelin basic protein-specific cytotoxic T cell lines from multiple sclerosis patients and healthy individuals", *J. immunol.* 145(2):540-548 (1990)

McCluskie, M. J. and Weeratna, R. D. 2001. Novel adjuvant systems. *Current Drug Targets-Infectious Disorders* 1:263-271.

McIntosh, T. K., "Novel pharmacologic therapies in the treatment of experimental traumatic brain injury: a review", *J. Neurotrauma* 10(3):215-261 (1993)

Meldrum, "Glutamate as a neurotransmitter in the brain: review of physiology and pathology", *J. Nutr.* 130: (4S Suppl):1007s-1015S (2000)

Netea M G, Brouwer A E, Hoogendoorn E H, Van der Meer J W, Koolen M, Verweij P E, Kullberg B J. 2004. Two patients with cryptococcal meningitis and idiopathic CD4 lymphopenia: defective cytokine production and reversal by recombinant interferon-gamma therapy. *Clin Infect Dis.* November 1; 39(9):e83-7.

Ota et al, "T-cell recognition of an immunodominant myelin basic protein epitope in multiple sclerosis", Nature 346 (6280):183-187 (1990)

Ouaaz, F., Arron, J., Zheng, Y., Choi, Y., Beg, A. A. 2002. Dendritic cell development and survival require distinct NF-κ B subunits. *Immunity* 16,257-270.

Pereira E F, Reinhardt-Maelicke S, Schrattenholz A, Maelicke A, Albuquerque E X. 1993. Identification and functional characterization of a new agonist site on nicotinic acetylcholine receptors of cultured hippocampal neurons. *J Pharmacol Exp Ther.* June; 265(3):1474-91.

Pette et al, "Myelin basic protein-specific T lymphocyte lines from MS patients and healthy individuals", *Proc. Natl. Acad. Sci. USA* 87(2):7968-7972 (1990)

Peyrottes S, Egron D, Lefebvre I, Gosselin G, Imbach J L, Perigaud C. 2004. SATE pronucleotide approaches: an overview. *Mini Rev Med Chem.* May; 4(4):395-408.

Pitt et al., "Glutamate excitotoxicity in a model of multiple sclerosis", *Nat Med,* 6:67-70 (2000)

Quaranta M G, Mattioli B, Giordani L, Viora M. 2004. HIV-1 Nef equips dendritic cells to reduce survival and function of CD8+ T cells: a mechanism of immune evasion. *FASEB J.* September; 18(12):1459-61.

Rapalino et al, "Implantation of stimulated homologous macrophages results in partial recovery of paraplegic rats", *Nat. Med.* 4(7):814-821 (1998)

Redlinger R E Jr, Shimizu T, Remy T, Alber S, Watkins S C, Barksdale E M Jr. 2003. Cellular mechanisms of interleukin-12-mediated neuroblastoma regression. *J Pediatr Surg.* February; 38(2):199-204.

Rimoldi M, Chieppa M, Vulcano M, Allavena P, Rescigno M. 2004. Intestinal epithelial cells control dendritic cell function. *Ann N Y Acad Sci.* December; 1029:66-74.

Sallusto F, Lanzavecchia A. 1994. Efficient presentation of soluble antigen by cultured human dendritic cells is maintained by granulocyte/macrophage colony-stimulating factor plus interleukin 4 and downregulated by tumor necrosis factor alpha. *J Exp Med.* April 1; 179(4):1109-18.

Sallusto, F., Palermo, B., Lenig, D., Miettinen, M., Matikainen, S., Julkunen, I., Forster, R., Burgstahler, R., Lipp, M., Lanzavecchia, A. 1999. Distinct patterns and kinetics of chemokine production regulate dendritic cell function. *Eur. J. Immunol.* 29,1617-1625.

Scandella E, Men Y, Gillessen S, Forster R, Groettrup M. 2002. Prostaglandin E2 is a key factor for CCR7 surface expression and migration of monocyte-derived dendritic cells. *Blood.* August 15; 100(4):1354-61.

Schluesener et al, "Autoaggressive T lymphocyte lines recognizing the encephalitogenic region of myelin basic protein: in vitro selection from unprimed rat T lymphocyte populations", *J. Immunol.* 135(5); 3128-3133 (1985)

Schoepp et al., "Pharmacological agents acting at subtypes of metabotropic glutamate receptors", *Neuropharmacology,* 38:1431-76 (1999)

Sewell, A. K., Price, D. A. 2001. Dendritic cells and transmission of HIV-1. *Trends Immunol.* 22,173-175.

Shimizu T, Berhanu A, Redlinger R E Jr, Watkins S, Lotze M T, Barksdale E M Jr. 2001. Interleukin-12 transduced dendritic cells induce regression of established murine neuroblastoma. *J Pediatr Surg.* August; 36(8):1285-92.

Shutt, D. C., Daniels, K. J., Carolan, E. J., Hill, A. C., Soll, D. R. 2000. Changes in the motility, morphology, and F-actin architecture of human dendritic cells in an in vitro model of dendritic cell development. *Cell Motil. Cytoskeleton* 46,200-221.

Stoll G, Jander S, Schroeter M. 2000. Cytokines in CNS disorders: neurotoxicity versus neuroprotection. *J Neural Transm Suppl.* 59:81-9.

Streilein, J. W., "Immune privilege as the result of local tissue barriers and immunosuppressive microenvironments", *Curr. Opin. Immunol.* 5(3):428-423 (1993)

Streilein, J. W., "Unraveling immune privilege", *Science* 270 (5239):1158-1159 (1995)

Swartz, M. 2003. Neuroprotection as a treatment for glaucoma: pharmacological and immunological approaches. *Eur J Ophthalmol.* April; 13 Suppl 3:S27-31.

Swartz, M. 2004. Vaccination for glaucoma: dream or reality? *Brain Res Bull.* February 15; 62(6):481-4.

Tomioka H. 2004. Adjunctive immunotherapy of mycobacterial infections. *Curr Pharm Des.* 10(26):3297-312.

Vives E, Dell'Aquila C, Bologna J C, Morvan F, Rayner B, Imbach J L. 1999. Lipophilic pro-oligonucleotides are rapidly and efficiently internalized in HeLa cells. *Nucleic Acids Res.* October 15; 27(20):4071-6.

Weigel B J, Rodeberg D A, Krieg A M, Blazar B R. 2003. CpG oligodeoxynucleotides potentiate the antitumor effects of chemotherapy or tumor resection in an orthotopic murine model of rhabdomyosarcoma. *Clin Cancer Res.* August 1; 9(8):3105-14.

Werkele, H., in The Blood-Brain Barrier, Pardridge, Ed., Raven Press, Ltd. New York, pp. 67-85 (1993)

Wu, D. et al, *J. Neurochem.* 62:37-44 (1994)

Yoshina, A. et al, *Brain Res.* 561:106-119 (1991)

Zelenay, S., Elias, F. and Flo, J. 2003. Immunostimulatory effects of plasmid DNA and synthetic oligonucleotides. *Eur J Immunol* 33:1382-92.

Zhang D, Yang X, Lu H, Zhong G, Brunham R C. 1999. Immunity to *Chlamydia trachomatis* mouse pneumonitis induced by vaccination with live organisms correlates with early granulocyte-macrophage colony-stimulating factor and interleukin-12 production and with dendritic cell-like maturation. *Infect Immun.* April; 67(4):1606-13.

Zivin et al, "Stroke therapy", *Sci. Am.* 265(1):56-63 (1991)

What is claimed is:

1. A method for modulating immune or inflammatory response in a patient, comprising administering an effective amount of cyclic di-GMP or a cyclic dinucleotide analogue thereof to a patient in need thereof to modulate the immune or inflammatory response.

2. The method of claim 1, comprising administering an effective amount of cyclic di-GMP or a cyclic dinucleotide analogue thereof to a patient in need thereof to stimulate or enhance the immune or inflammatory response in the patient.

3. The method of claim 2, wherein an effective amount of cyclic di-GMP is administered to the patient in need thereof.

4. The method of claim 2, wherein an effective amount of a cyclic dinucleotide analogue is administered to the patient in need thereof.

5. The method of claim 4, wherein said cyclic dinucleotide analogue thereof is selected from the group consisting of cyclic dinucleotide compounds (I)-(XX)

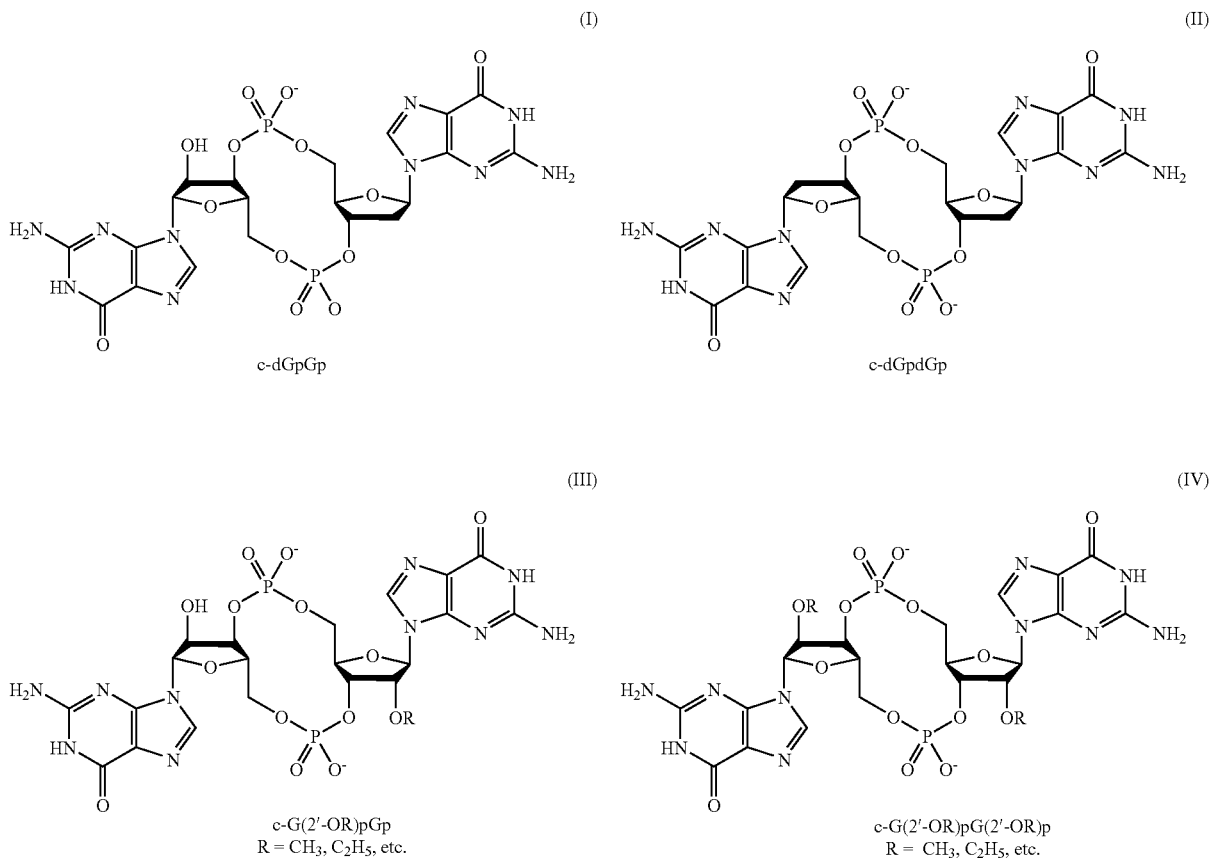

-continued
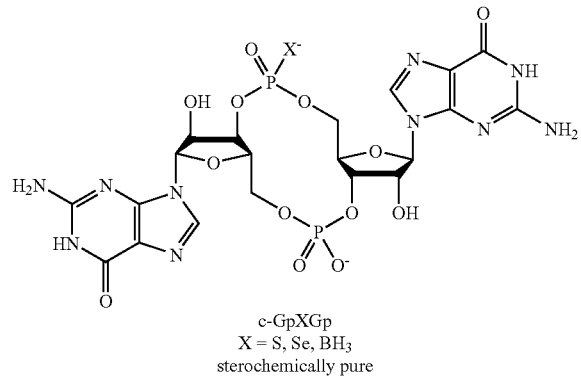
c-GpXGp
X = S, Se, BH₃
sterochemically pure
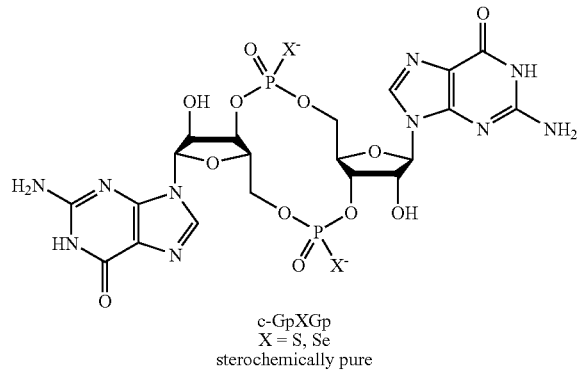
c-GpXGp
X = S, Se
sterochemically pure
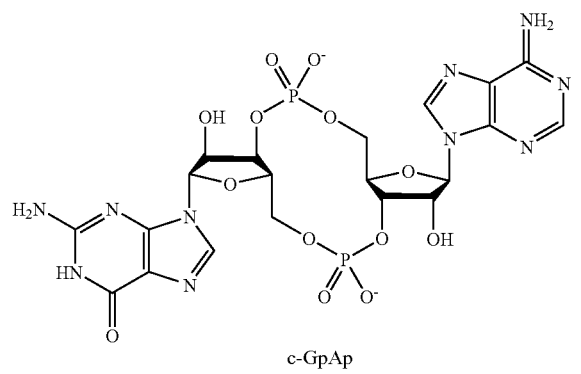
c-GpAp
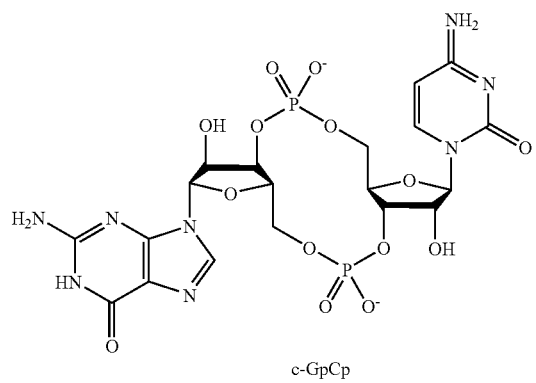
c-GpCp
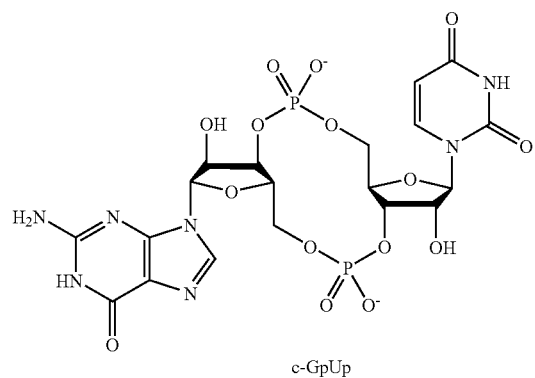
c-GpUp
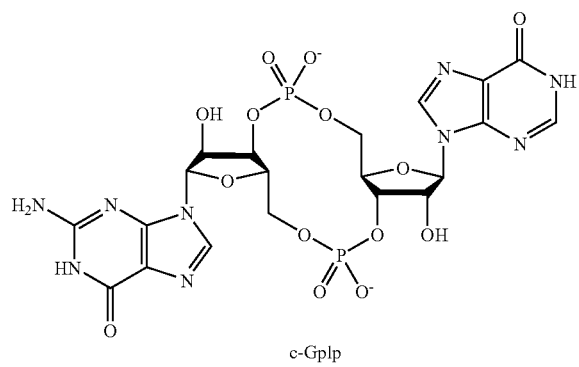
c-GpIp
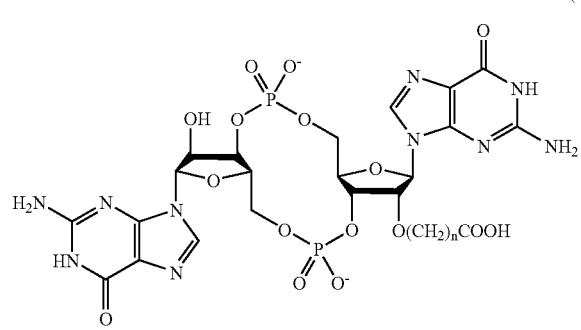
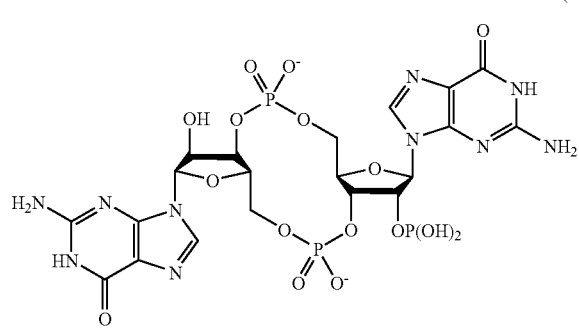

-continued
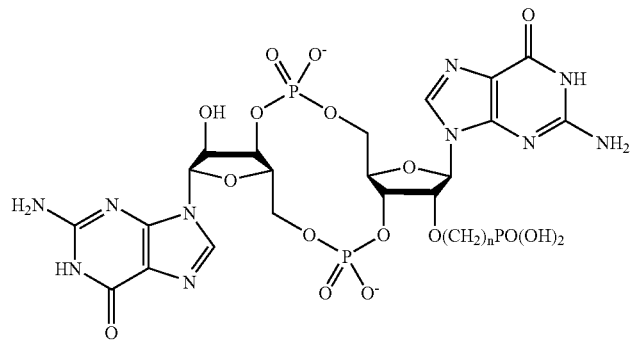
(XIII)
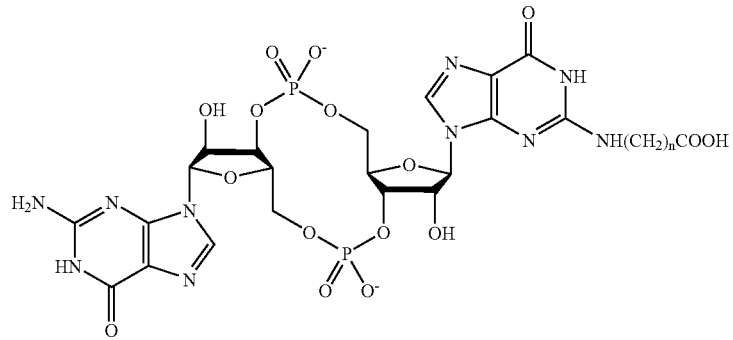
(XIV)
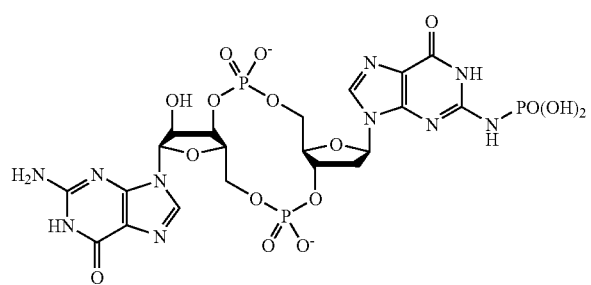
(XV)
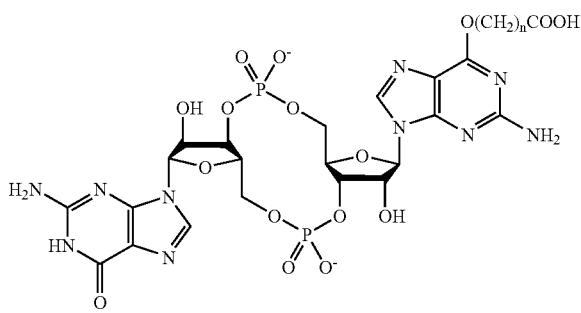
(XVI)
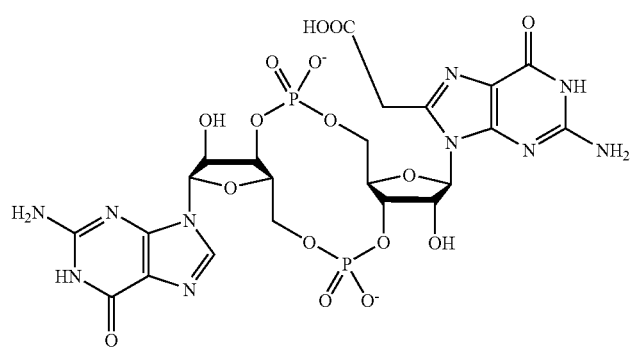
(XVII)

-continued

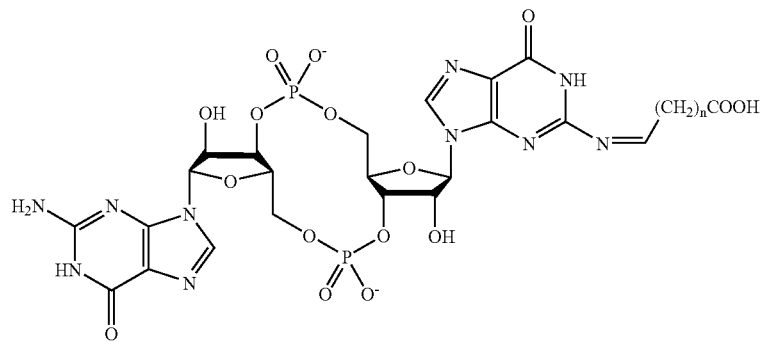
(XVIII)

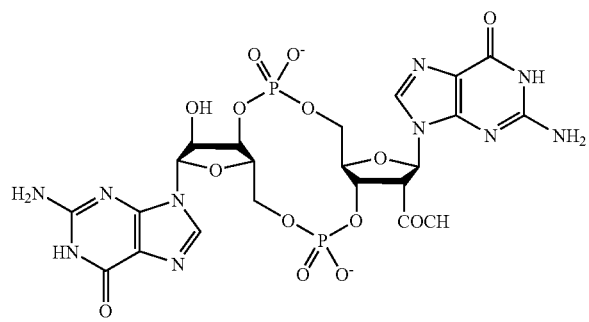
(XIX)

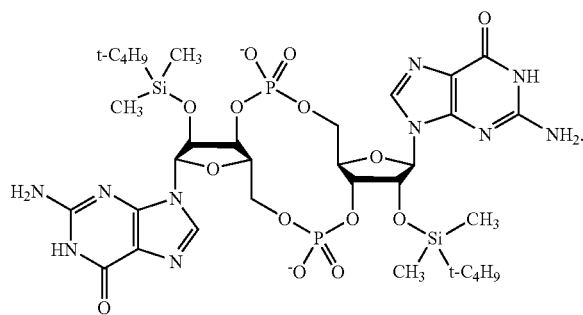
(XX)

2'-O-TBDMS-c-di-GMP

6. The method of claim 2, wherein the immune response stimulated or enhanced includes a Th1 oriented immune response.

7. The method of claim 2, which enhances immune response to a vaccine, wherein an effective amount of a vaccine or antigen is administered to the patient in need thereof in combination with an effective amount of cyclic di-GMP or a cyclic dinucleotide analogue thereof.

8. The method of claim 7, wherein the immune response is a cellular response.

9. The method of claim 7, wherein the vaccine is selected from the group consisting of a protein vaccine, a polysaccharide vaccine, a DNA vaccine, a live attenuated vaccine, and a killed vaccine.

10. A method for inhibiting neuronal degeneration, comprising administering to a patient in need thereof an effective amount of cyclic di-GMP or a cyclic dinucleotide analogue thereof to inhibit neuronal degeneration in the patient.

11. The method of claim 10, wherein an effective amount of cyclic di-GMP is administered to the patient in need thereof.

12. The method of claim 10, wherein an effective amount of a cyclic dinucleotide analogue is administered to the patient in need thereof.

13. The method of claim 12, wherein said cyclic dinucleotide analogue thereof is selected from the group consisting of cyclic dinucleotide compounds (I)-(XX)

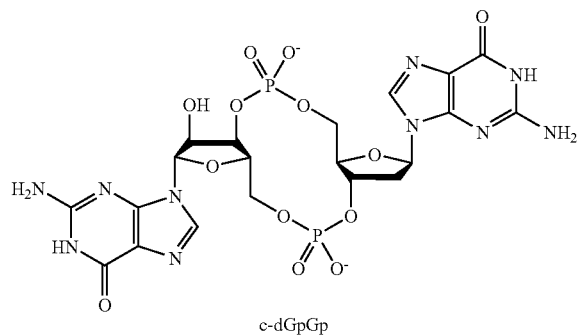
(I)

c-dGpGp

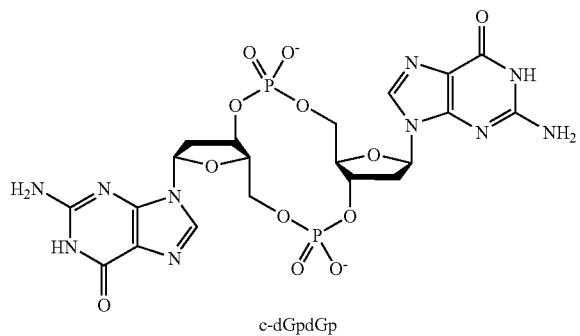
(II)

c-dGpdGp

-continued
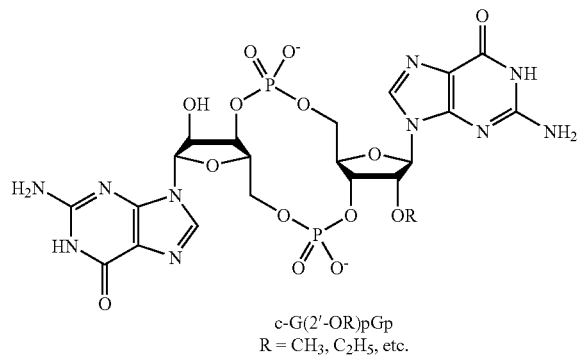
c-G(2'-OR)pGp
R = CH$_3$, C$_2$H$_5$, etc.
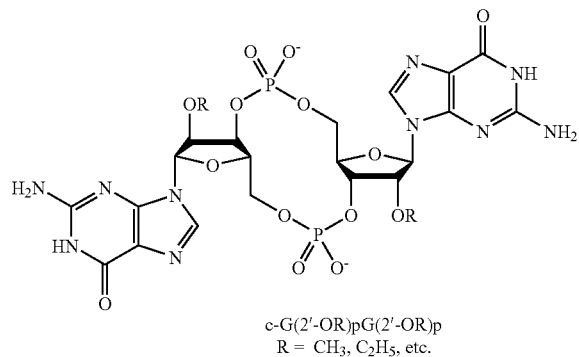
c-G(2'-OR)pG(2'-OR)p
R = CH$_3$, C$_2$H$_5$, etc.
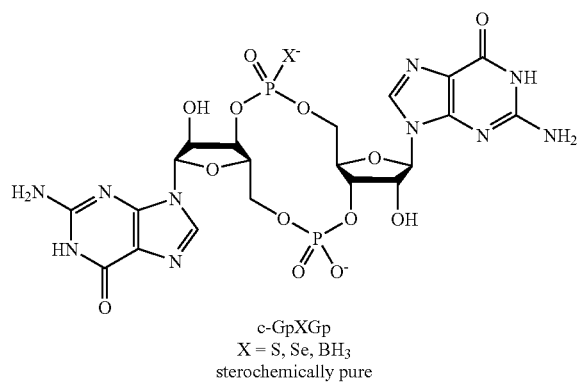
c-GpXGp
X = S, Se, BH$_3$
sterochemically pure
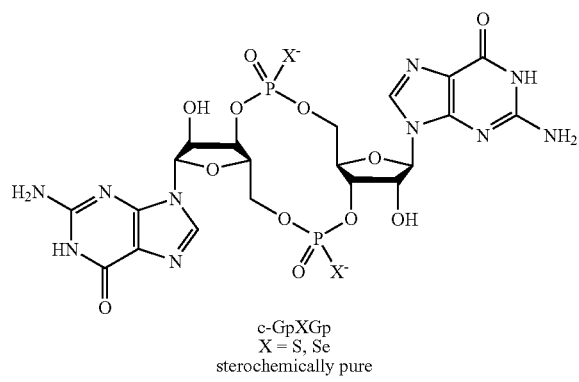
c-GpXGp
X = S, Se
sterochemically pure
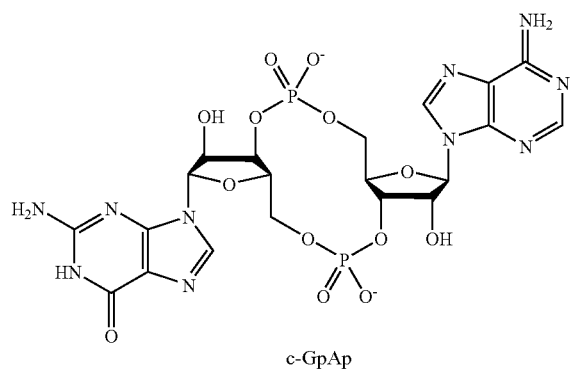
c-GpAp
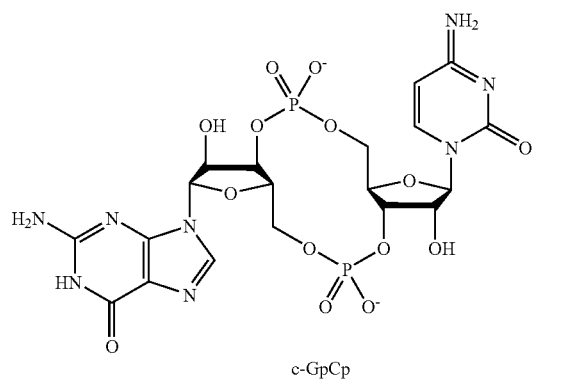
c-GpCp
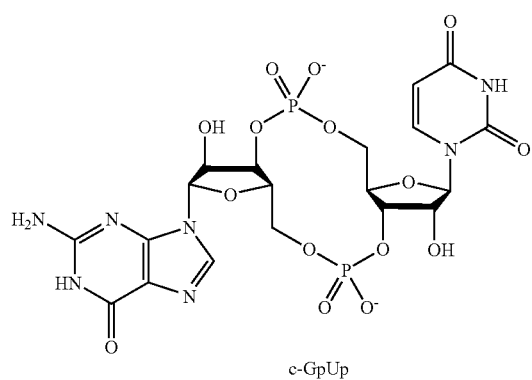
c-GpUp
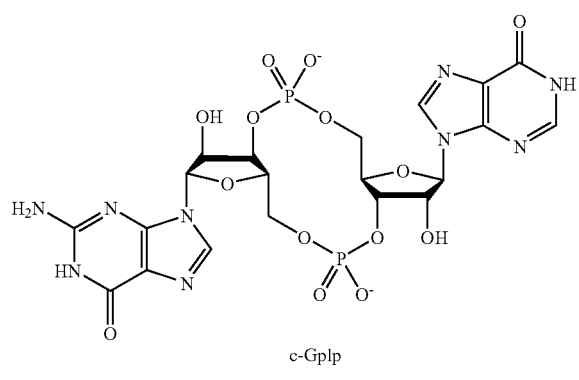
c-GpIp -continued
(XI)
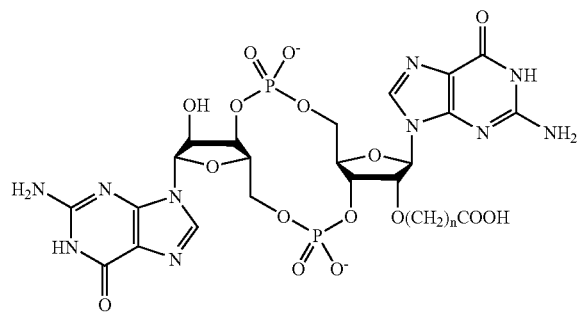
(XII)
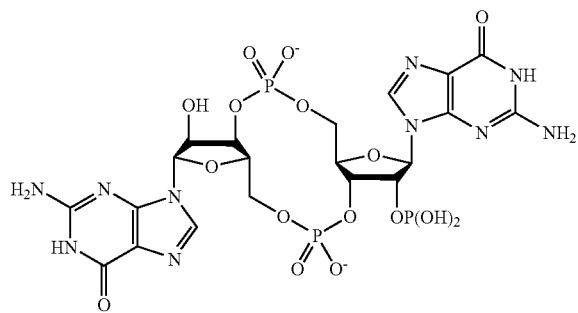
(XIII)
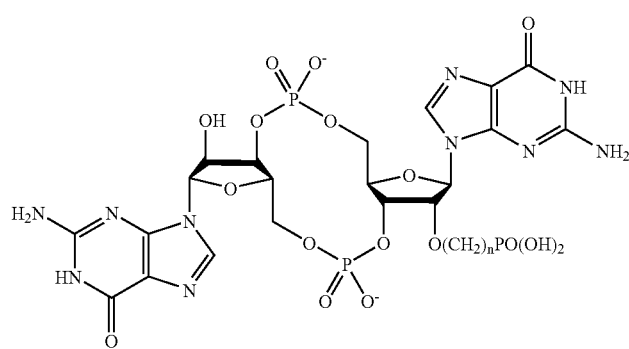
(XIV)
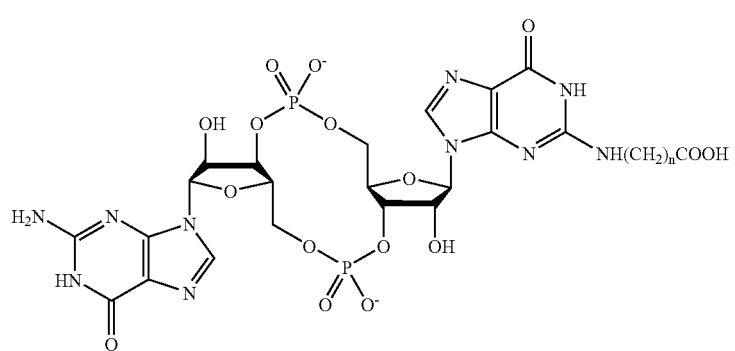
(XV)
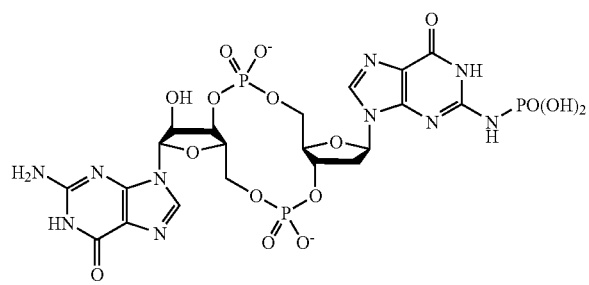
(XVI)
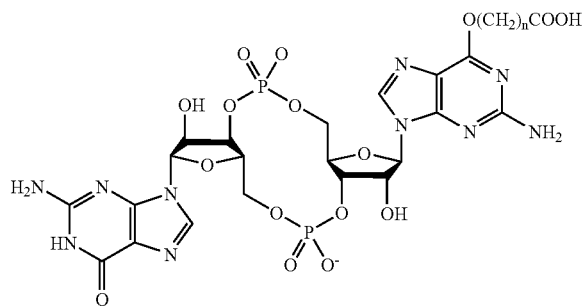

-continued
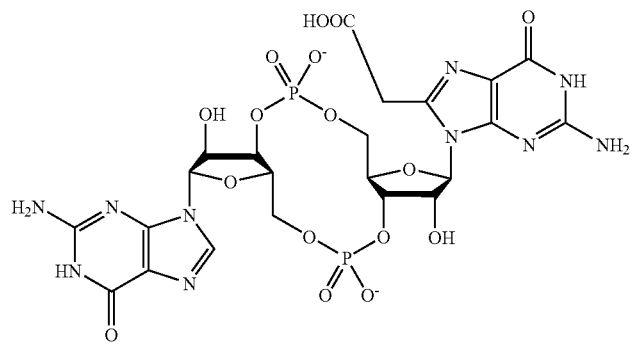
(XVII)
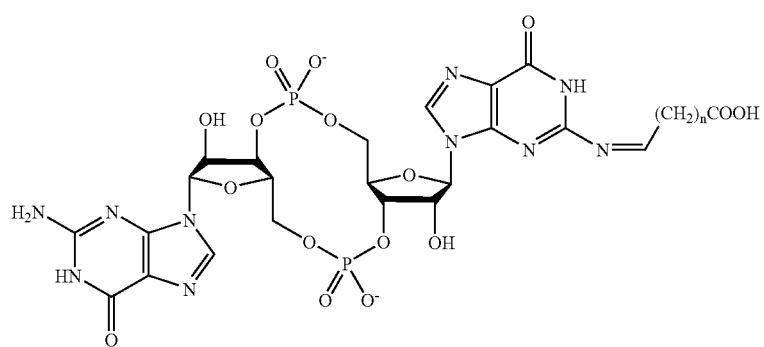
(XVIII)
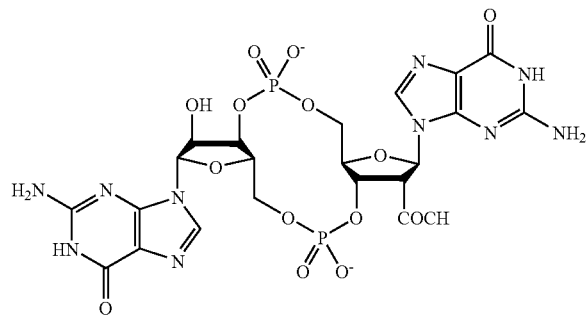
(XIX)
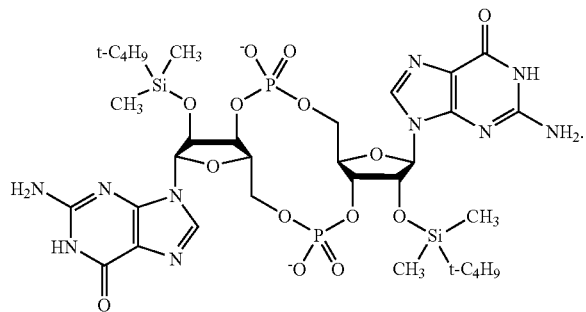
(XX)
2'-O-TBDMS-c-di-GMP

14. The method of claim 1, comprising administering an effective amount of cyclic di-GMP or a cyclic dinucleotide analogue thereof to a patient in need thereof to inhibit an allergic reaction.

15. The method of claim 14, wherein an effective amount of cyclic di-GMP is administrated to the patient in need thereof.

16. The method of claim 14, wherein an effective amount of a cyclic dinucleotide analogue of cyclic di-GMP is administered to the patient in need thereof.

17. The method of claim 16, wherein said cyclic dinucleotide analogue is selected from the group consisting of cyclic dinucleotide compounds (I)-(XX)

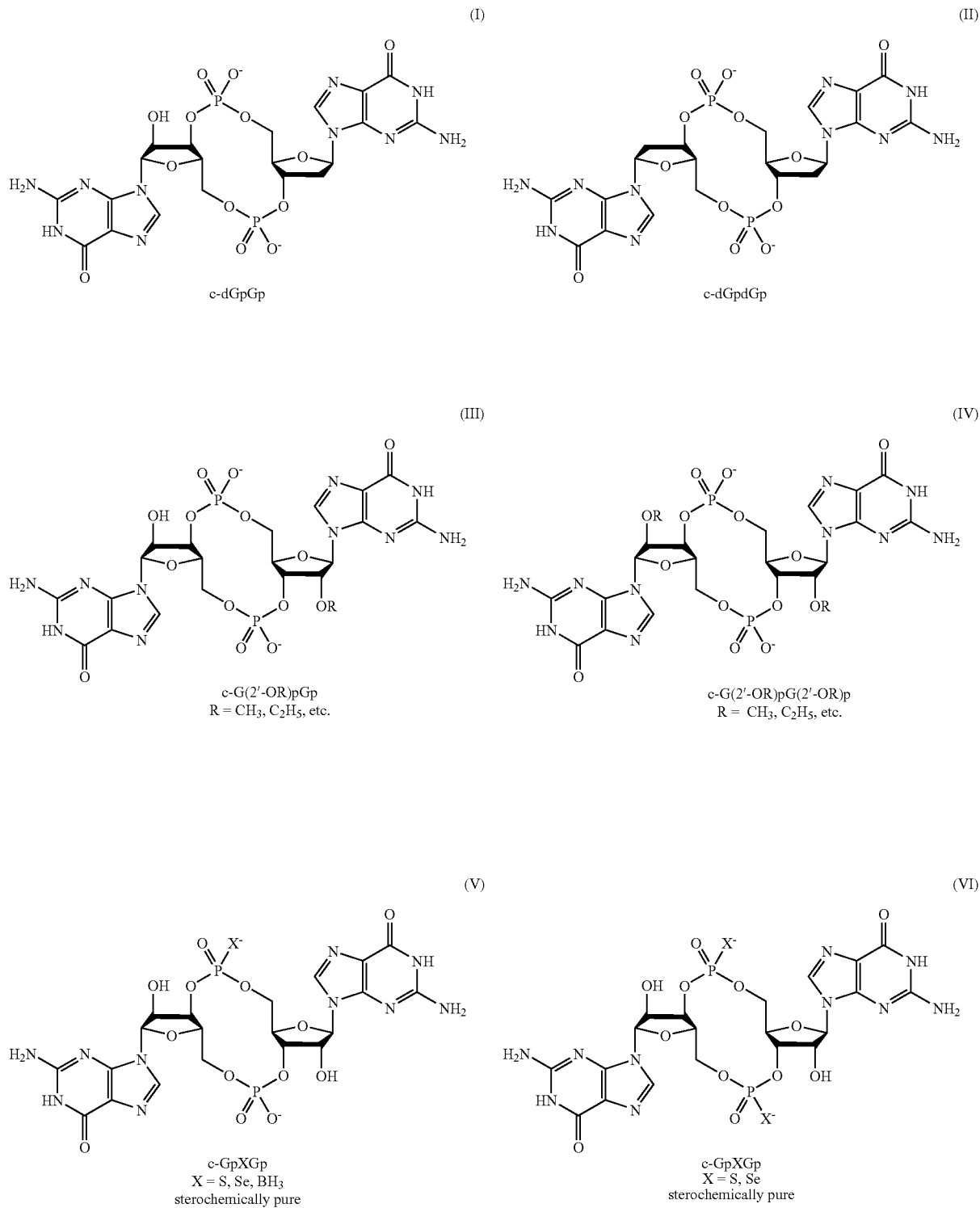

-continued
(VII)
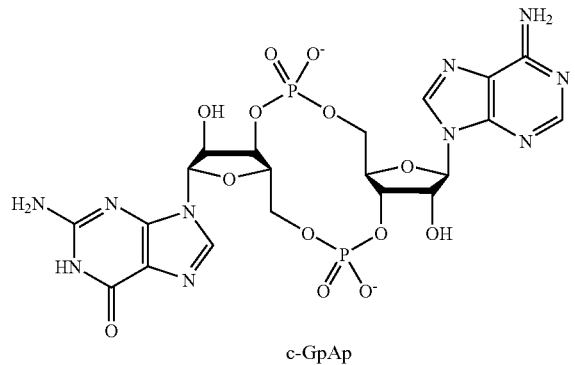
c-GpAp
(VIII)
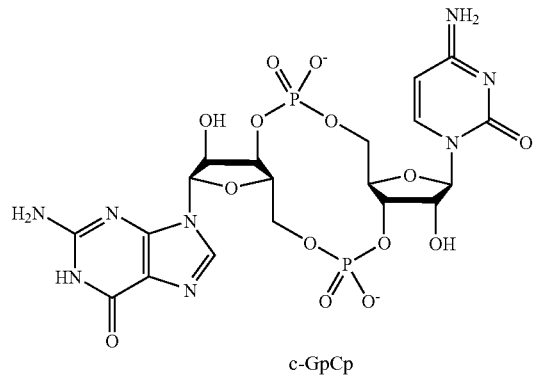
c-GpCp
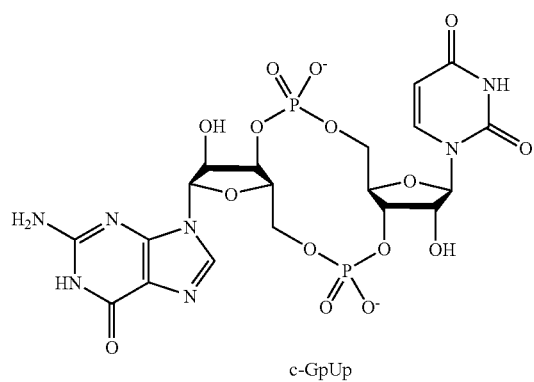
c-GpUp
(X)
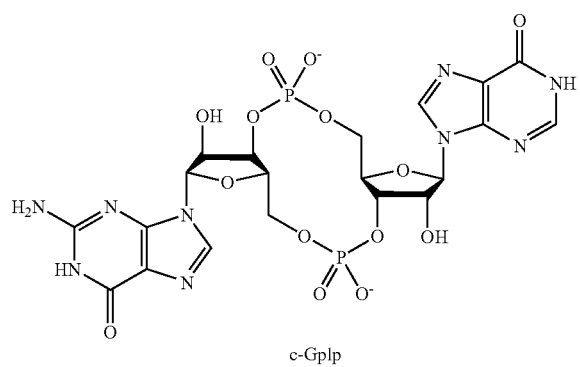
c-GpIp
(XI)
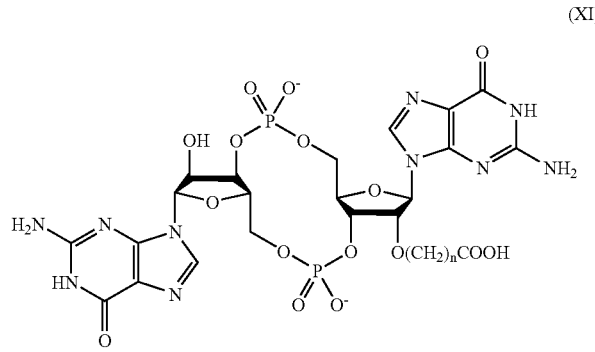
(XII)
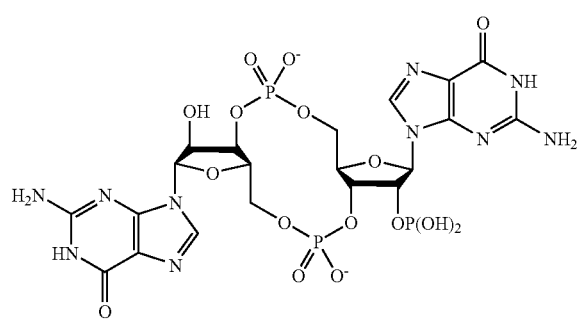
(XIII)
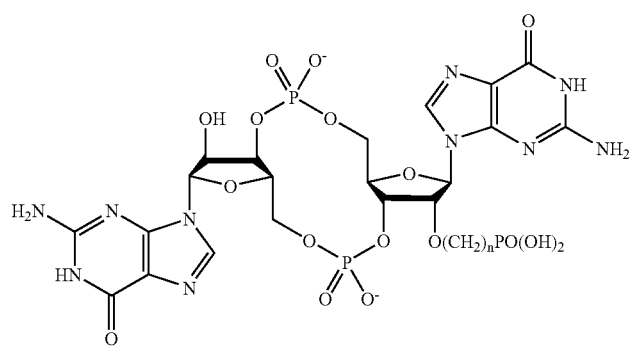

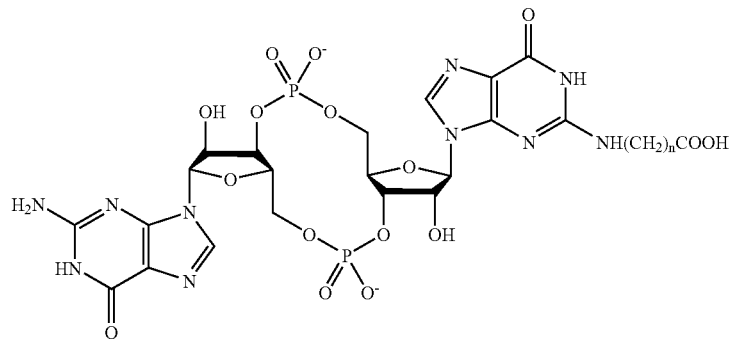
(XIV)
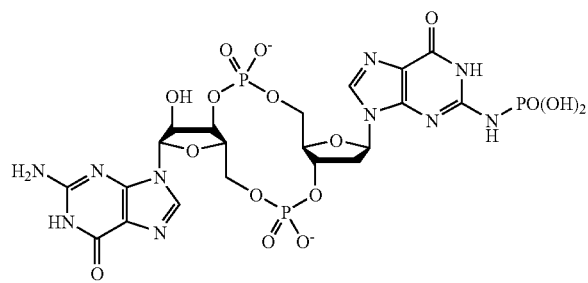
(XV)
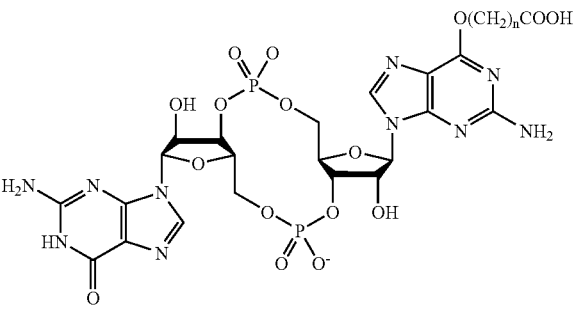
(XVI)
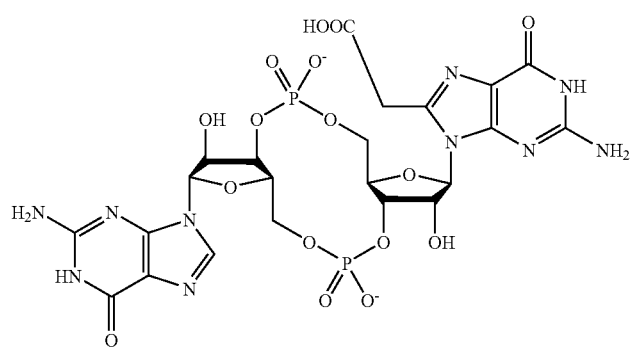
(XVII)
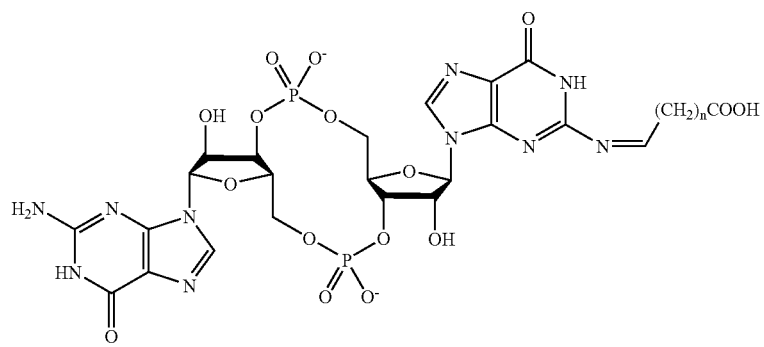
(XVIII)

-continued
(XIX)
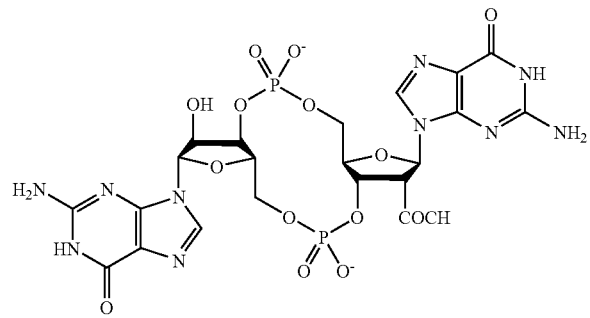
(XX)
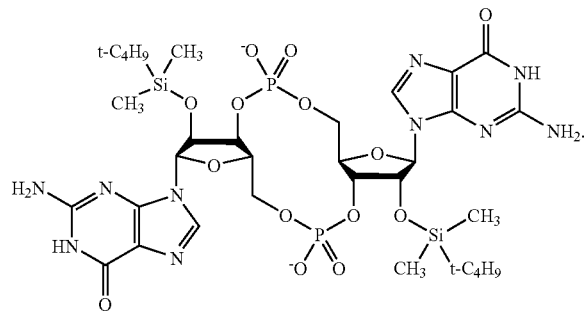
2′-O-TBDMS-c-di-GMP
* * * * *